(12) United States Patent
Hissong et al.

(10) Patent No.: US 12,414,779 B2
(45) Date of Patent: Sep. 16, 2025

(54) DEVICES AND TECHNIQUES FOR PERFORMING AN OSTEOTOMY PROCEDURE ON A FIRST METATARSAL TO CORRECT A BONE MISALIGNMENT

(71) Applicant: Treace Medical Concepts, Inc., Ponte Vedra, FL (US)

(72) Inventors: Tyler Hissong, Jacksonville, FL (US); Joe W. Ferguson, Ponte Vedra Beach, FL (US); Lowell Weil, Jr., Lake Forest, IL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 311 days.

(21) Appl. No.: 17/844,675

(22) Filed: Jun. 20, 2022

(65) Prior Publication Data

US 2022/0313277 A1    Oct. 6, 2022

Related U.S. Application Data

(63) Continuation of application No. 16/812,487, filed on Mar. 9, 2020, now Pat. No. 11,364,037, which is a
(Continued)

(51) Int. Cl.
*A61B 17/14*    (2006.01)
*A61B 17/15*    (2006.01)
(Continued)

(52) U.S. Cl.
CPC ............ *A61B 17/151* (2013.01); *A61B 17/14* (2013.01); *A61B 17/152* (2013.01); *A61B 17/1682* (2013.01); *A61B 17/1775* (2016.11)

(58) Field of Classification Search
CPC .. A61B 17/151; A61B 17/152; A61B 17/1775
See application file for complete search history.

(56) References Cited

U.S. PATENT DOCUMENTS 2,557,364 A    6/1951    Tillson
2,737,835 A  *  3/1956    Herz ................. A61B 17/8863
                                                      72/457
(Continued)

FOREIGN PATENT DOCUMENTS

AU    2009227957 B2    7/2014
CA       2491824 A1    9/2005
(Continued)

OTHER PUBLICATIONS

"Accu-Cut Osteotomy Guide System," BioPro, Brochure, Oct. 2018, 2 pages.
(Continued)

*Primary Examiner* — Christian A Sevilla
(74) *Attorney, Agent, or Firm* — Fredrikson & Byron, P.A.

(57) ABSTRACT

Devices and techniques for adjusting an alignment for a first metatarsal may include making a plurality of cuts along the length of the first metatarsal. In different applications of the technique, a plurality of transverse cuts may or may not be made intersecting the longitudinal cuts. In either case, the cuts can separate the first metatarsal into two individual portions and release a removable wedge of bone. The different portions of the metatarsal can be moved relative to each other to adjust an anatomical alignment of one portion relative to another portion, for example in multiple planes. After suitably adjusting the alignment of the different bone portions, the portions can be fixed together.

20 Claims, 15 Drawing Sheets

Related U.S. Application Data continuation of application No. 15/809,298, filed on Nov. 10, 2017, now Pat. No. 10,582,936.

(60) Provisional application No. 62/421,027, filed on Nov. 11, 2016.

(51) Int. Cl.
*A61B 17/16* (2006.01)
*A61B 17/17* (2006.01)

(56) References Cited

U.S. PATENT DOCUMENTS

| | | | |
|---|---|---|---|
| 3,159,952 A | 12/1964 | Lipkins | |
| 4,069,824 A | 1/1978 | Weinstock | |
| 4,159,716 A | 7/1979 | Borchers | |
| 4,187,840 A | 2/1980 | Watanabe | |
| 4,335,715 A | 6/1982 | Kirkley | |
| 4,338,927 A | 7/1982 | Volkov et al. | |
| 4,349,018 A | 9/1982 | Chambers | |
| 4,409,973 A | 10/1983 | Neufeld | |
| 4,440,168 A | 4/1984 | Warren | |
| 4,501,268 A | 2/1985 | Comparetto | |
| 4,502,474 A | 3/1985 | Comparetto | |
| 4,509,511 A | 4/1985 | Neufeld | |
| 4,565,191 A | 1/1986 | Slocum | |
| 4,570,624 A | 2/1986 | Wu | |
| 4,627,425 A | 12/1986 | Reese | |
| 4,628,919 A | 12/1986 | Clyburn | |
| 4,632,102 A | 12/1986 | Comparetto | |
| 4,664,102 A | 5/1987 | Comparetto | |
| 4,677,973 A | 7/1987 | Slocum | |
| 4,708,133 A | 11/1987 | Comparetto | |
| 4,750,481 A | 6/1988 | Reese | |
| 4,754,746 A | 7/1988 | Cox | |
| 4,757,810 A | 7/1988 | Reese | |
| 4,787,908 A | 11/1988 | Wyss et al. | |
| 4,895,141 A | 1/1990 | Koeneman et al. | |
| 4,952,214 A * | 8/1990 | Comparetto | A61B 17/15 606/82 |
| 4,978,347 A | 12/1990 | Ilizarov | |
| 4,988,349 A | 1/1991 | Pennig | |
| 4,995,875 A | 2/1991 | Coes | |
| 5,021,056 A | 6/1991 | Hofmann et al. | |
| 5,035,698 A | 7/1991 | Comparetto | |
| 5,042,983 A | 8/1991 | Rayhack | |
| 5,049,149 A | 9/1991 | Schmidt | |
| 5,053,039 A | 10/1991 | Hofmann et al. | |
| 5,078,719 A | 1/1992 | Schreiber | |
| 5,112,334 A | 5/1992 | Alchermes et al. | |
| 5,147,364 A | 9/1992 | Comparetto | |
| 5,176,685 A | 1/1993 | Rayhack | |
| 5,207,676 A | 5/1993 | Canadell et al. | |
| 5,246,444 A | 9/1993 | Schreiber | |
| 5,254,119 A | 10/1993 | Schreiber | |
| 5,312,412 A | 5/1994 | Whipple | |
| 5,358,504 A | 10/1994 | Paley et al. | |
| 5,364,402 A | 11/1994 | Mumme et al. | |
| 5,413,579 A | 5/1995 | Tom Du Toit | |
| 5,417,694 A | 5/1995 | Marik et al. | |
| 5,449,360 A | 9/1995 | Schreiber | |
| 5,470,335 A | 11/1995 | Du Toit | |
| 5,490,854 A | 2/1996 | Fisher et al. | |
| 5,529,075 A | 6/1996 | Clark | |
| 5,540,695 A | 7/1996 | Levy | |
| 5,578,038 A | 11/1996 | Slocum | |
| 5,586,564 A | 12/1996 | Barrett et al. | |
| 5,601,565 A | 2/1997 | Huebner | |
| 5,613,969 A | 3/1997 | Jenkins, Jr. | |
| 5,620,442 A | 4/1997 | Bailey et al. | |
| 5,620,448 A | 4/1997 | Puddu | |
| 5,643,270 A | 7/1997 | Combs | |
| 5,667,510 A | 9/1997 | Combs | |
| H1706 H | 1/1998 | Mason | |
| 5,722,978 A | 3/1998 | Jenkins | |
| 5,749,875 A | 5/1998 | Puddu | |
| 5,765,648 A | 6/1998 | Sheehan et al. | |
| 5,779,709 A | 7/1998 | Harris et al. | |
| 5,788,695 A | 8/1998 | Richardson | |
| 5,803,924 A | 9/1998 | Oni et al. | |
| 5,810,822 A | 9/1998 | Mortier | |
| 5,843,085 A | 12/1998 | Graser | |
| 5,893,553 A | 4/1999 | Pinkous | |
| 5,911,724 A | 6/1999 | Wehrli | |
| 5,928,234 A | 7/1999 | Manspeizer | |
| 5,935,128 A | 8/1999 | Carter et al. | |
| 5,941,877 A | 8/1999 | Viegas et al. | |
| 5,951,556 A | 9/1999 | Faccioli et al. | |
| 5,980,526 A | 11/1999 | Johnson et al. | |
| 5,984,931 A | 11/1999 | Greenfield | |
| 6,007,535 A | 12/1999 | Rayhack et al. | |
| 6,027,504 A | 2/2000 | Mcguire | |
| 6,030,391 A | 2/2000 | Brainard et al. | |
| 6,162,223 A | 12/2000 | Orsak et al. | |
| 6,171,309 B1 | 1/2001 | Huebner | |
| 6,203,545 B1 | 3/2001 | Stoffella | |
| 6,248,109 B1 | 6/2001 | Stoffella | |
| 6,391,031 B1 | 5/2002 | Toomey | |
| 6,478,799 B1 | 11/2002 | Williamson | |
| 6,511,481 B2 | 1/2003 | Von Hoffmann et al. | |
| 6,547,793 B1 | 4/2003 | McGuire | |
| 6,676,662 B1 | 1/2004 | Bagga et al. | |
| 6,719,773 B1 | 4/2004 | Boucher et al. | |
| 6,743,233 B1 | 6/2004 | Baldwin et al. | |
| 6,755,838 B2 | 6/2004 | Trnka | |
| 6,796,986 B2 | 9/2004 | Duffner | |
| 6,859,661 B2 | 2/2005 | Tuke | |
| 7,018,383 B2 | 3/2006 | McGuire | |
| 7,033,361 B2 | 4/2006 | Collazo | |
| 7,097,647 B2 | 8/2006 | Segler et al. | |
| 7,112,204 B2 | 9/2006 | Justin et al. | |
| 7,153,310 B2 | 12/2006 | Ralph et al. | |
| 7,182,766 B1 | 2/2007 | Mogul | |
| 7,241,298 B2 | 7/2007 | Nemec et al. | |
| 7,282,054 B2 | 10/2007 | Steffensmeier et al. | |
| 7,377,924 B2 | 5/2008 | Raistrick et al. | |
| 7,465,303 B2 | 12/2008 | Riccione et al. | |
| 7,540,874 B2 | 6/2009 | Trumble et al. | |
| 7,572,258 B2 | 8/2009 | Stiernborg | |
| 7,641,660 B2 | 1/2010 | Lakin et al. | |
| D610,257 S | 2/2010 | Horton | |
| 7,686,811 B2 | 3/2010 | Byrd et al. | |
| 7,691,108 B2 | 4/2010 | Lavallee | |
| 7,763,026 B2 | 7/2010 | Egger et al. | |
| D629,900 S | 12/2010 | Fisher | |
| 7,967,823 B2 | 6/2011 | Ammann et al. | |
| 7,972,338 B2 | 7/2011 | O'Brien | |
| D646,389 S | 10/2011 | Claypool et al. | |
| 8,057,478 B2 | 11/2011 | Kuczynski et al. | |
| 8,062,301 B2 | 11/2011 | Ammann et al. | |
| D651,315 S | 12/2011 | Bertoni et al. | |
| D651,316 S | 12/2011 | May et al. | |
| 8,080,010 B2 | 12/2011 | Schulz et al. | |
| 8,083,746 B2 | 12/2011 | Novak | |
| 8,123,753 B2 | 2/2012 | Poncet | |
| 8,137,406 B2 | 3/2012 | Novak et al. | |
| 8,147,530 B2 | 4/2012 | Strnad et al. | |
| 8,167,918 B2 | 5/2012 | Strnad et al. | |
| 8,172,848 B2 | 5/2012 | Tomko et al. | |
| 8,192,441 B2 | 6/2012 | Collazo | |
| 8,197,487 B2 | 6/2012 | Poncet et al. | |
| 8,231,623 B1 | 7/2012 | Jordan | |
| 8,231,663 B2 | 7/2012 | Kay et al. | |
| 8,236,000 B2 | 8/2012 | Ammann et al. | |
| 8,246,561 B1 | 8/2012 | Agee et al. | |
| D666,721 S | 9/2012 | Wright et al. | |
| 8,262,664 B2 | 9/2012 | Justin et al. | |
| 8,277,459 B2 | 10/2012 | Sand et al. | |
| 8,282,644 B2 | 10/2012 | Edwards | |
| 8,282,645 B2 | 10/2012 | Lawrence et al. | |
| 8,292,966 B2 | 10/2012 | Morton | |
| 8,303,596 B2 | 11/2012 | Plassky et al. | |
| 8,313,492 B2 | 11/2012 | Wong et al. | |
| 8,323,289 B2 | 12/2012 | Re | |

(56) References Cited

U.S. PATENT DOCUMENTS

| | | | |
|---|---|---|---|
| 8,337,503 B2 | 12/2012 | Lian | |
| 8,343,159 B2 | 1/2013 | Bennett | |
| 8,377,105 B2 | 2/2013 | Bscher | |
| D679,395 S | 4/2013 | Wright et al. | |
| 8,409,209 B2 | 4/2013 | Ammann et al. | |
| 8,435,246 B2 | 5/2013 | Fisher et al. | |
| 8,475,462 B2 | 7/2013 | Thomas et al. | |
| 8,496,662 B2 | 7/2013 | Novak et al. | |
| 8,518,045 B2 | 8/2013 | Szanto | |
| 8,523,870 B2 | 9/2013 | Green et al. | |
| 8,529,571 B2 | 9/2013 | Horan et al. | |
| 8,535,317 B2 | 9/2013 | Szanto | |
| 8,540,777 B2 * | 9/2013 | Ammann | A61B 17/68 623/20.32 |
| D694,884 S | 12/2013 | Mooradian et al. | |
| D695,402 S | 12/2013 | Dacosta et al. | |
| 8,652,142 B2 | 2/2014 | Geissler | |
| 8,657,820 B2 * | 2/2014 | Kubiak | A61B 17/809 606/70 |
| D701,303 S | 3/2014 | Cook | |
| 8,672,945 B2 | 3/2014 | Lavallee et al. | |
| 8,696,716 B2 | 4/2014 | Kartalian et al. | |
| 8,702,715 B2 | 4/2014 | Ammann et al. | |
| D705,929 S | 5/2014 | Frey | |
| 8,715,363 B2 | 5/2014 | Ratron et al. | |
| 8,728,084 B2 | 5/2014 | Berelsman et al. | |
| 8,758,354 B2 | 6/2014 | Habegger et al. | |
| 8,764,760 B2 | 7/2014 | Metzger et al. | |
| 8,764,763 B2 | 7/2014 | Wong et al. | |
| 8,771,279 B2 | 7/2014 | Philippon et al. | |
| 8,777,948 B2 | 7/2014 | Bernsteiner | |
| 8,784,427 B2 | 7/2014 | Fallin et al. | |
| 8,784,457 B2 | 7/2014 | Graham | |
| 8,795,286 B2 | 8/2014 | Sand et al. | |
| 8,801,727 B2 | 8/2014 | Chan et al. | |
| 8,808,303 B2 | 8/2014 | Stemniski et al. | |
| 8,828,012 B2 | 9/2014 | May et al. | |
| 8,858,602 B2 | 10/2014 | Weiner et al. | |
| 8,882,778 B2 | 11/2014 | Ranft | |
| 8,882,816 B2 | 11/2014 | Kartalian et al. | |
| 8,888,785 B2 | 11/2014 | Ammann et al. | |
| D720,456 S | 12/2014 | Dacosta et al. | |
| 8,900,247 B2 | 12/2014 | Tseng et al. | |
| 8,906,026 B2 | 12/2014 | Ammann et al. | |
| 8,915,922 B2 | 12/2014 | Fitzpatrick et al. | |
| 8,945,132 B2 | 2/2015 | Plassky et al. | |
| 8,998,903 B2 | 4/2015 | Price et al. | |
| 8,998,904 B2 | 4/2015 | Zeetser et al. | |
| D730,132 S | 5/2015 | Szanto | |
| 9,023,052 B2 | 5/2015 | Lietz et al. | |
| 9,044,250 B2 | 6/2015 | Olsen et al. | |
| 9,060,822 B2 | 6/2015 | Lewis et al. | |
| 9,089,376 B2 | 7/2015 | Medoff et al. | |
| 9,101,421 B2 | 8/2015 | Blacklidge | |
| 9,107,715 B2 | 8/2015 | Blitz et al. | |
| 9,113,920 B2 | 8/2015 | Ammann et al. | |
| D740,424 S | 10/2015 | Dacosta et al. | |
| 9,427,240 B2 | 8/2016 | Von Zabern et al. | |
| D765,844 S | 9/2016 | DaCosta | |
| D766,434 S | 9/2016 | DaCosta | |
| D766,437 S | 9/2016 | DaCosta | |
| D766,438 S | 9/2016 | DaCosta | |
| D766,439 S | 9/2016 | DaCosta | |
| 9,452,057 B2 | 9/2016 | Dacosta et al. | |
| 9,750,538 B2 | 9/2017 | Soffiatti et al. | |
| 9,750,551 B1 | 9/2017 | Nichols | |
| 9,785,747 B2 | 10/2017 | Geebelen | |
| 9,980,760 B2 | 5/2018 | Dacosta et al. | |
| 10,028,750 B2 | 7/2018 | Rose | |
| 10,064,631 B2 | 9/2018 | Dacosta et al. | |
| 10,159,499 B2 | 12/2018 | Dacosta et al. | |
| 10,292,713 B2 | 5/2019 | Fallin et al. | |
| 10,327,829 B2 | 6/2019 | Dacosta et al. | |
| 10,376,268 B2 | 8/2019 | Fallin et al. | |
| 10,582,936 B1 * | 3/2020 | Hissong | A61B 17/151 |
| 11,304,705 B2 | 4/2022 | Fallin et al. | |
| 11,364,037 B2 * | 6/2022 | Hissong | A61B 17/152 |
| 2002/0099381 A1 | 7/2002 | Maroney | |
| 2002/0107519 A1 | 8/2002 | Dixon et al. | |
| 2002/0165552 A1 | 11/2002 | Duffner | |
| 2002/0198531 A1 | 12/2002 | Millard et al. | |
| 2004/0010259 A1 | 1/2004 | Keller et al. | |
| 2004/0039394 A1 | 2/2004 | Conti et al. | |
| 2004/0065117 A1 | 4/2004 | Chen et al. | |
| 2004/0097946 A1 | 5/2004 | Dietzel et al. | |
| 2004/0138669 A1 | 7/2004 | Horn | |
| 2005/0004676 A1 | 1/2005 | Schon et al. | |
| 2005/0059978 A1 | 3/2005 | Sherry et al. | |
| 2005/0070909 A1 | 3/2005 | Egger et al. | |
| 2005/0075641 A1 | 4/2005 | Singhatat et al. | |
| 2005/0101961 A1 | 5/2005 | Huebner et al. | |
| 2005/0149042 A1 | 7/2005 | Metzger | |
| 2005/0228389 A1 | 10/2005 | Stiernborg | |
| 2005/0251147 A1 | 11/2005 | Novak | |
| 2005/0267482 A1 | 12/2005 | Hyde | |
| 2005/0273112 A1 | 12/2005 | McNamara | |
| 2006/0015102 A1 | 1/2006 | Toullec et al. | |
| 2006/0129163 A1 | 6/2006 | McGuire | |
| 2006/0206044 A1 | 9/2006 | Simon | |
| 2006/0217733 A1 | 9/2006 | Plassky et al. | |
| 2006/0229621 A1 | 10/2006 | Cadmus | |
| 2006/0241607 A1 | 10/2006 | Myerson et al. | |
| 2006/0241608 A1 | 10/2006 | Myerson et al. | |
| 2006/0264961 A1 | 11/2006 | Murray-Brown | |
| 2007/0010818 A1 | 1/2007 | Stone et al. | |
| 2007/0123857 A1 | 5/2007 | Deffenbaugh et al. | |
| 2007/0233138 A1 | 10/2007 | Figueroa et al. | |
| 2007/0244487 A1 * | 10/2007 | Ammann | A61B 17/68 606/88 |
| 2007/0265634 A1 | 11/2007 | Weinstein | |
| 2007/0276383 A1 | 11/2007 | Rayhack | |
| 2008/0009863 A1 | 1/2008 | Bond et al. | |
| 2008/0039850 A1 | 2/2008 | Rowley et al. | |
| 2008/0091197 A1 | 4/2008 | Coughlin | |
| 2008/0140081 A1 | 6/2008 | Heavener et al. | |
| 2008/0147073 A1 | 6/2008 | Ammann et al. | |
| 2008/0172054 A1 | 7/2008 | Claypool et al. | |
| 2008/0195215 A1 | 8/2008 | Morton | |
| 2008/0208252 A1 | 8/2008 | Holmes | |
| 2008/0262500 A1 | 10/2008 | Collazo | |
| 2008/0269908 A1 | 10/2008 | Warburton | |
| 2009/0036893 A1 | 2/2009 | Kartalian et al. | |
| 2009/0036931 A1 | 2/2009 | Pech et al. | |
| 2009/0054899 A1 | 2/2009 | Ammann et al. | |
| 2009/0093849 A1 | 4/2009 | Grabowski | |
| 2009/0105767 A1 | 4/2009 | Reiley | |
| 2009/0118733 A1 | 5/2009 | Orsak et al. | |
| 2009/0198244 A1 | 8/2009 | Leibel | |
| 2009/0198279 A1 | 8/2009 | Zhang et al. | |
| 2009/0222047 A1 | 9/2009 | Graham | |
| 2009/0254092 A1 | 10/2009 | Albiol Llorach | |
| 2009/0254126 A1 | 10/2009 | Orbay et al. | |
| 2009/0287309 A1 | 11/2009 | Walch et al. | |
| 2010/0069910 A1 | 3/2010 | Hasselman | |
| 2010/0121334 A1 | 5/2010 | Couture et al. | |
| 2010/0130981 A1 | 5/2010 | Richards | |
| 2010/0152782 A1 | 6/2010 | Stone et al. | |
| 2010/0168799 A1 | 7/2010 | Schumer | |
| 2010/0185245 A1 | 7/2010 | Paul et al. | |
| 2010/0249779 A1 | 9/2010 | Hotchkiss et al. | |
| 2010/0256687 A1 | 10/2010 | Neufeld et al. | |
| 2010/0274293 A1 | 10/2010 | Terrill et al. | |
| 2010/0318088 A1 | 12/2010 | Warne et al. | |
| 2010/0324556 A1 | 12/2010 | Tyber et al. | |
| 2011/0093084 A1 | 4/2011 | Morton | |
| 2011/0245835 A1 | 10/2011 | Dodds et al. | |
| 2011/0264149 A1 | 10/2011 | Pappalardo et al. | |
| 2011/0288550 A1 | 11/2011 | Orbay et al. | |
| 2011/0301648 A1 | 12/2011 | Lofthouse et al. | |
| 2012/0016426 A1 | 1/2012 | Robinson | |
| 2012/0065689 A1 | 3/2012 | Prasad et al. | |
| 2012/0078258 A1 | 3/2012 | Lo et al. | |
| 2012/0123420 A1 | 5/2012 | Honiball | |
| 2012/0123484 A1 | 5/2012 | Lietz et al. | |

(56) References Cited

U.S. PATENT DOCUMENTS

| | | |
|---|---|---|
| 2012/0130376 A1 | 5/2012 | Loring et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0056031 A1 | 3/2017 | Awtrey et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2018/0110530 A1 | 4/2018 | Wagner et al. |
| 2018/0132868 A1 | 5/2018 | Dacosta et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 1457968 A | 11/2003 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 2255312 A1 | 5/1974 |
| DE | 4425456 A1 | 3/1996 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2304322 A1 | 10/1976 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |

(56) References Cited

FOREIGN PATENT DOCUMENTS

| | | |
|---|---|---|
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 | 2/2013 |
| IN | 2004/KOLP/2013 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2074810 C1 | 3/1997 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

"Acumed Osteotomiesystem Operationstechnik," Acumed, 2014, 19 pages (including 3 pages English translation).
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
"Futura Forefoot Implant Arthroplasty Products," Tornier, Inc., 2008, 14 pages.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
"Hat-Trick Lesser Toe Repair System, Foot and Ankle Technique Guide, Metatarsal Shortening Osteotomy Surgical Technique," Smith & Nephew, 2014, 16 pages.

Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Otsuki et al., "Developing a novel custom cutting guide for curved per-acetabular osteotomy," International Orthopaedics (SICOT), vol. 37, 2013, pp. 1033-1038.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
"Smith & Nephew scores a Hat-Trick with its entry into the high-growth hammer toe repair market," Smith & Nephew, Jul. 31, 2014, 2 pages.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Anderson et al., "Uncemented STAR Total Ankle Prostheses," The Journal of Bone and Joint Surgery, vol. 86(1, Suppl 2), Sep. 2004, pp. 103-111, (Abstract Only).

(56) References Cited

OTHER PUBLICATIONS

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System For Navigation Of Bone Alignment Osteotomies Of The Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Dayton et al."Evidence-Based Bunion Surgery: A Critical Examination of Current and Emerging Concepts and Techniques," Springer International Publishing, 2017, 254 pages.
Joung et al., "A spherical bone cutting system for Rotational Acetabular Osteotomy," World Congress on Medical Physics and Biomedical Engineering, 2006, pp. 3130-3133 (Abstract Only).
Koyama et al., "Computer-assisted spherical osteotomy with a curved-bladed Tuke Saw®," Computer Aided Surgery, vol. 11, No. 4, Jul. 2006, pp. 202-208.
Sakuma et al., "A bone cutting device for rotational acetabular osteotomy (RAO) with a curved oscillating saw," International Congress Series, vol. 1268, 2004, pp. 632-637.

(56) References Cited

OTHER PUBLICATIONS

Weil Foot & Ankle Institute, "Scarf Akin Procedure for Bunion Correction," YouTube video, published on Jul. 29, 2008 to https://www.youtube.com/watch?v=Sh2V8QvbaGc, 4 pages of example screen shots.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, US Pat. U.S. Appl. No. 62/118,378, filed Feb. 19, 2015, 62 pages.
Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.

(56) References Cited

OTHER PUBLICATIONS

Schon et al., "Cuneiform-Metatarsal Arthrodesis for Hallux Valgus," The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.

(56) References Cited

OTHER PUBLICATIONS

Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

* cited by examiner

DEVICES AND TECHNIQUES FOR PERFORMING AN OSTEOTOMY PROCEDURE ON A FIRST METATARSAL TO CORRECT A BONE MISALIGNMENT

CROSS-REFERENCE

This application is a continuation of U.S. patent application Ser. No. 16/812,487, filed Mar. 9, 2020, and issued as U.S. Pat. No. 11,364,037 on Jun. 21, 2022, which is a continuation of U.S. patent application Ser. No. 15/809,298, filed Nov. 10, 2017, and issued as U.S. Pat. No. 10,582,936 on Mar. 10, 2020, which claims priority to U.S. Provisional Patent Application No. 62/421,027, filed Nov. 11, 2016. The entire contents of each of these applications are incorporated herein by reference.

TECHNICAL FIELD

This disclosure relates to devices and techniques for correcting bones and, more particularly, to osteotomy techniques for correcting bone misalignment.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to devices and techniques for correcting an anatomical misalignment of one or more bones. In some examples, the devices and techniques are utilized to correct a misalignment of a first metatarsal relative to a medial cuneiform and/or an adjacent second metatarsal, such as bunion correction procedure. To perform a corrective procedure, a clinician may make two parallel but offset cuts along the length of the first metatarsal. The two cuts may be angled relative to each other across the thickness of the bone, causing the cuts to intersect to form a wedged-shaped section of bone. If the cuts do not extend the entire length of the bone, the clinician can further make two transverse cuts on opposite ends of the longitudinal cuts, e.g., adjacent the proximal and distal ends of the first metatarsal, to release the wedge-shaped section of bone from a remainder of the metatarsal. The transverse cuts can be made before, after, or between making each of the two longitudinal cuts.

Upon resecting the wedge-shaped section of bone from the first metatarsal, the first metatarsal may be divided into two independently movable portions. In cases where the first metatarsal is cut with longitudinal and transverse cuts, the metatarsal may be divided into a proximal portion connected to the medial cuneiform and a distal portion connected to the proximal phalanx. In cases where the first metatarsal is along the longitudinal axis but without transverse cuts, the metatarsal may be divided into a plantar portion and a dorsal portion. In either case, clinician can move the two portions of the first metatarsal relative to each other in multiple planes to help correct the anatomical misalignment of the first metatarsal (e.g., the distal portion of the first metatarsal). For example, the clinician may rotate one portion of the first metatarsal in the frontal plane, pivot the portion of the first metatarsal in the transverse plane, and/or pivot the portion of the first metatarsal in the sagittal plane to adjust the anatomical alignment of the one portion of the first metatarsal relative to the other portion of the first metatarsal.

In some applications, the clinician removes the wedge portion cut from the first metatarsal to provide clearance for realignment. This can enable one portion of the metatarsal (e.g., the distal portion) to be rotated relative to the other portion of the first metatarsal (e.g., the proximal portion). In some examples, a clinician may also trim around the perimeter of the cut end of the distal portion and/or proximal portion of the first metatarsal, e.g., to avoid causing the rotated bone portion to create an interfering lip or edge where it is rotated out of plane.

The clinician may or may not use the wedge-shaped bone portion resected from the first metatarsal as an autograft to fill a space created during realignment of one portion of the cut first metatarsal relative to another portion of the cut metatarsal. For example, the wedge-shaped bone portion may be resected from the medial side of the first metatarsal to create a space that allows for realignment of a first portion of the metatarsal relative to a second portion of the metatarsal. For example, a distal portion of the first metatarsal may be moved in one or more planes (e.g., the frontal plane) relative to the proximal portion, closing the space created by removal of the wedge-shaped bone portion. A corresponding gap may be created on the lateral side of the first metatarsal through realignment. The wedge-shaped bone portion can be inserted as an autograft in this gap. The clinician may or may not trim or otherwise resize the wedge-shaped bone portion to fit within the space created through realignment. Instead of reusing the bone portion harvested from the first metatarsal as an autograft, the clinician may use a different bone construct to fill the gap created through realignment, such as an allograft harvested from another person, a xenograft harvested from a different species, or synthetic bone.

Although different instruments may be used to perform the bone correction procedure, in some examples, a bone cutting guide is used that has a longitudinal cutting slot. In one example, the bone cutting guide has a longitudinal cutting slot and a plurality of fixation apertures to allow the guide to be fixated at different rotational and angular positions about the first metatarsal to be cut. Additionally or alternatively, the bone cutting may have one or more transverse cutting slots that extend upwardly and/or downwardly from the longitudinal cutting slot. For example, the bone cutting guide may include a longitudinal cutting slot, a first transverse cutting slot that intersects one end of the longitudinal cutting slot, and a second transverse cutting slot that intersects the opposite end of the longitudinal cutting slot. In use, a clinician may use the longitudinal cutting slot to cut along the length of the first metatarsal and, after rotating the cutting guide, use the longitudinal cutting slot to make a second, intersecting cut along the length of the first metatarsal. The clinician may further use the two transverse cutting slots to make intersecting cuts to the two longitudinal cuts (e.g., in the dorsal to plantar direction, or vice versa). This may cleave the first metatarsal into adjacent proximal and distal portions for realignment.

In one example, a method is described that includes making a first longitudinal cut through a first metatarsal between a proximal end of the first metatarsal and a distal end of the first metatarsal. The method also includes making a second longitudinal cut through the first metatarsal between a proximal end of the first metatarsal and a distal end of the first metatarsal, where the second longitudinal cut is radially offset from the first longitudinal cut and intersects the first longitudinal cut. The method further involves making a transverse cut adjacent the proximal end of the first metatarsal that intersects the first longitudinal cut and the second longitudinal cut and making a transverse cut adjacent the distal end of the first metatarsal that intersects the first longitudinal cut and the second longitudinal cut. In addition, the method includes removing a bone wedge from the first metatarsal and moving a distal portion of the first metatarsal relative to a proximal portion of the first metatarsal in at least two planes, thereby adjusting an anatomical alignment of the distal portion of the first metatarsal relative to the proximal portion of the first metatarsal.

In another example, a bone cutting guide is described that includes a body configured to be positioned against a bone to be cut. The body includes a longitudinal cutting slot having a first end and a second end, a first transverse cutting slot extending downwardly from the first end of the longitudinal cutting slot, and a second transverse cutting slot extending upwardly from the second end of the longitudinal cutting slot.

In another example, a bone cutting guide is described that includes a body having a length extending from a first end to a second end and that is sized to be positioned against a first metatarsal. The example specifies that the body includes a longitudinal cutting slot extending between the first end and the second end, a first securing projection extending substantially orthogonally relative to the length in one direction and containing at least one fixation aperture, and a second securing projection extending substantially orthogonally relative to the length in an opposite direction and containing at least one fixation aperture.

In another example, a method is described that includes making a first longitudinal cut through a first metatarsal extending from a proximal end of the first metatarsal to a distal end of the first metatarsal and making a second longitudinal cut extending from the proximal end of the first metatarsal to the distal end of the first metatarsal. The example specifies that the second longitudinal cut is radially offset from the first longitudinal cut and intersects the first longitudinal cut, thereby separating the first metatarsal into a first portion, a second portion, and a bone wedge. The technique involves removing the bone wedge from the first metatarsal and moving the first portion of the first metatarsal relative to the second portion of the first metatarsal, thereby adjusting an anatomical alignment of the first portion of the first metatarsal relative to the second portion of the first metatarsal.

The details of one or more examples are set forth in the accompanying drawings and the description below. Other features, objects, and advantages will be apparent from the description and drawings, and from the claims.

DETAILED DESCRIPTION

In general, the present disclosure is directed to devices and techniques for correcting a misalignment of one or more bones. The disclosed devices and techniques can be implemented in an osteotomy procedure in which a bone is surgically cut and/or a piece of bone is surgically removed. In some examples, the technique is performed on one or more bones in the foot or hand, where bones are relatively small compared to bones in other parts of the human anatomy. For example, the foregoing description generally refers to example techniques performed on the foot and, more particularly a metatarsal of the foot. However, the disclosed techniques may be performed on other bones, such as the tibia, fibula, ulna, humerus, femur, or yet other bone, and the disclosure is not limited in this respect unless otherwise specifically indicated. In some applications, however, the disclosed techniques are used to correct a misalignment between a metatarsal (e.g., a first metatarsal) and a second metatarsal and/or a cuneiform (e.g., a medial, or first, cuneiform), such as in a bunion correction surgery.

Figure 1B:
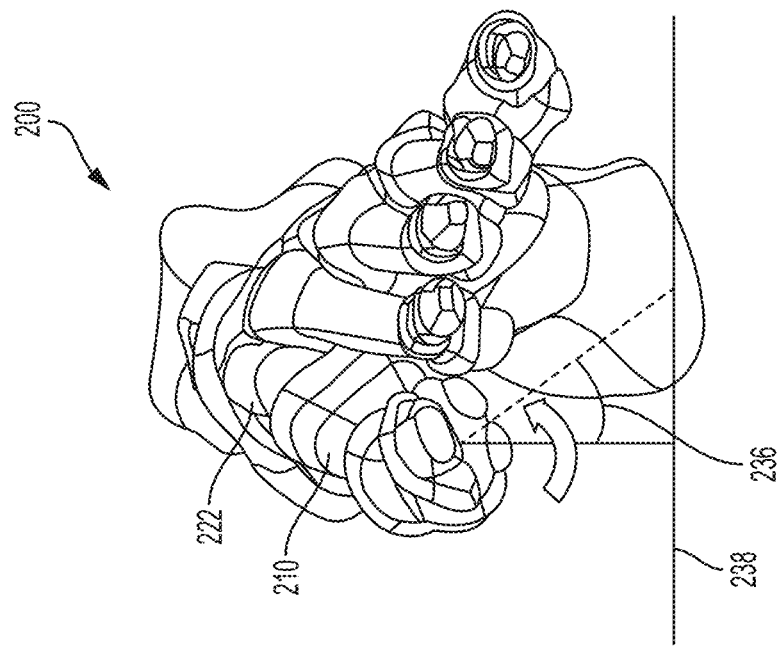
FIGS. 1A and 1B are front views of a foot showing a normal first metatarsal position and an example frontal plane rotational misalignment position, respectively.
Figure 1A:
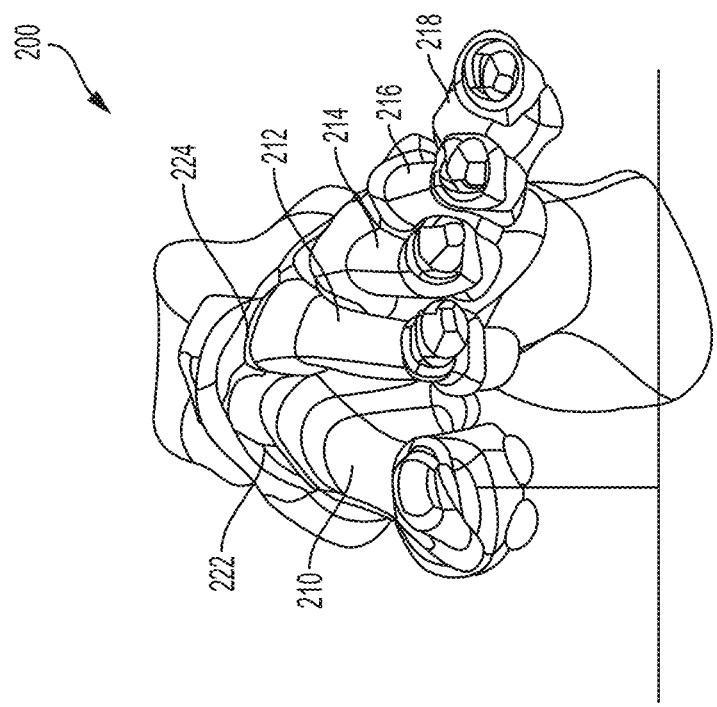
Figure 2B:
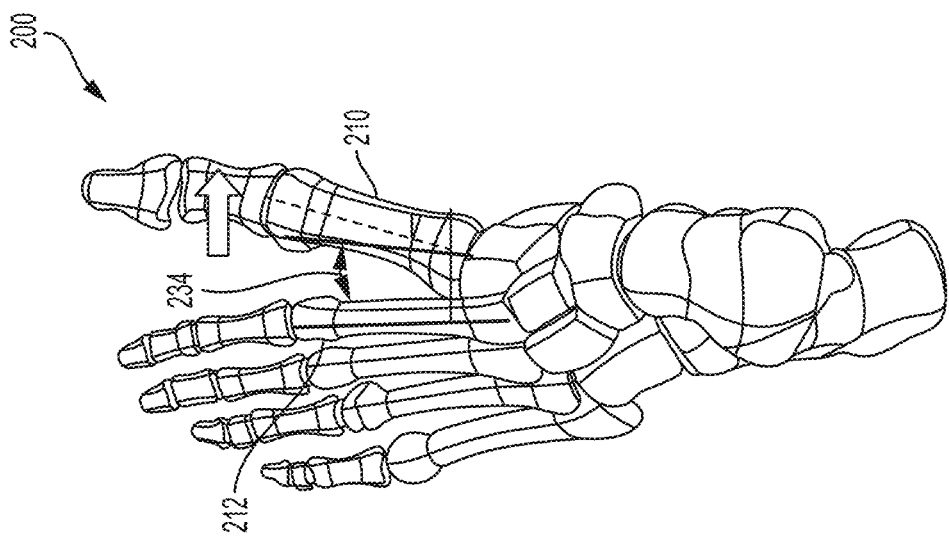
FIGS. 2A and 2B are top views of a foot showing a normal first metatarsal position and an example transverse plane misalignment position, respectively.
Figure 2A:
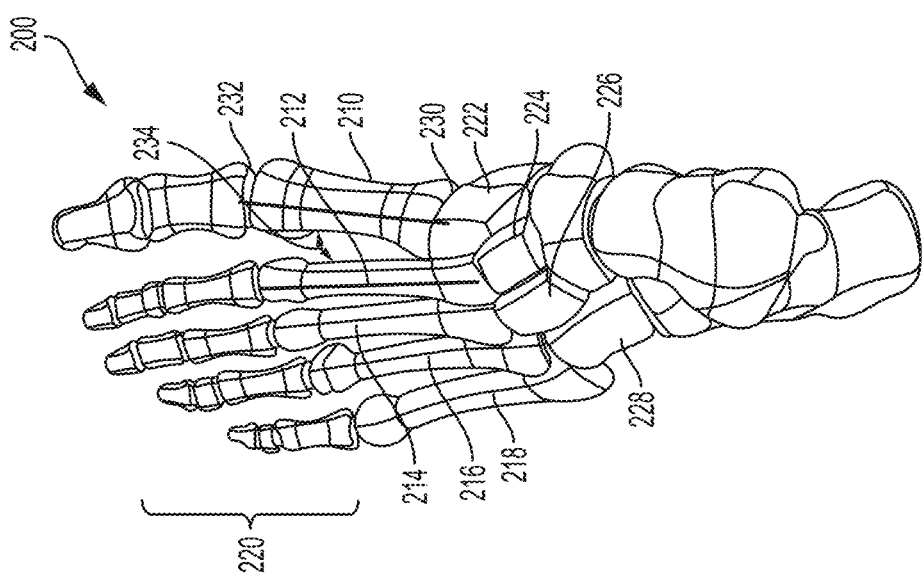

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS.

Figure 3B:
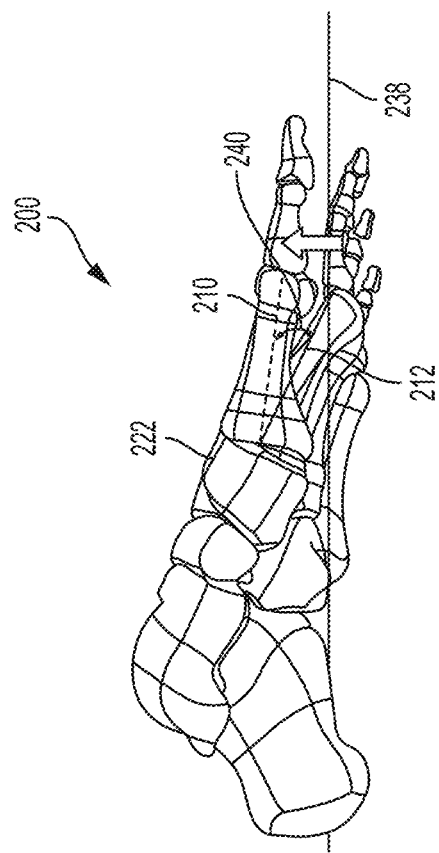
FIGS. 3A and 3B are side views of a foot showing a normal first metatarsal position and an example sagittal plane misalignment position, respectively.

3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

Figure 3A:
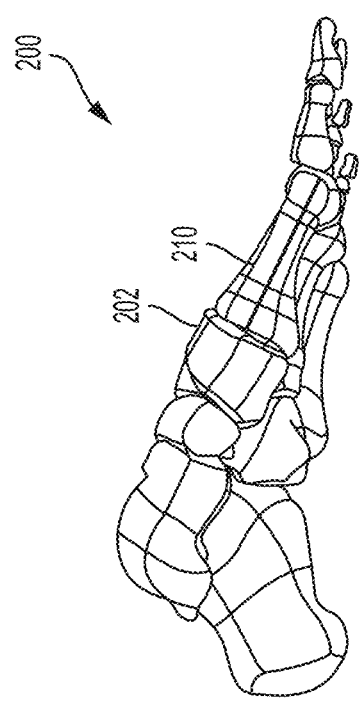

FIG. 3A is a side view of foot 200 showing a typical position of first metatarsal 210 in the sagittal plane. The sagittal plane is a plane parallel to the sagittal structure which divides the body into right and left halves. On foot 200, the sagittal plane is a plane that extends vertically and is perpendicular to an axis extending medially to laterally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

Bone positioning techniques and instruments according to the disclosure can be useful to correct an anatomical misalignment of a bones or bones. In some applications, the technique involves realigning a portion of a metatarsal relative to an adjacent metatarsal portion. The metatarsal undergoing realignment may be anatomically misaligned in the frontal plane, transverse plane, and/or sagittal plane, as illustrated and discussed with respect to FIGS. 1-3 above. Accordingly, realignment may involve cutting the metatarsal into two independently movable portions and thereafter realigning one metatarsal portion relative to the other metatarsal portion in one or more planes, two or more planes, or all three planes. After suitably realigning the metatarsal portions, the metatarsal portions can be fixated to hold and maintain the realigned positioned.

While a metatarsal can have a variety of anatomically aligned and misaligned positions, in some examples, the term "anatomically aligned position" means that an angle of a long axis of first metatarsal 210 or portion thereof relative to the long axis of second metatarsal 212 is about 10 degrees or less in the transverse plane and/or sagittal plane. In certain embodiments, anatomical misalignment can be corrected in both the transverse plane and the frontal plane. In the transverse plane, a normal IMA 234 between first metatarsal 210 or portion thereof and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods according to the disclosure are utilized to anatomically align first metatarsal 210 or a portion thereof by reducing the IMA from over 10 degrees to about 10 degrees or less (e.g., to an IMA of about 1-5 degrees), including to negative angles of about −5 degrees or until interference with the second metatarsal, by positioning the first metatarsal or portion thereof at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods according to the disclosure are utilized to anatomically align the metatarsal or portion thereof by reducing the metatarsal rotation from about 4 degrees or more to less than 4 degrees (e.g., to about 0 to 2 degrees) by rotating the metatarsal or portion thereof with respect to the medial cuneiform.

Figure 4:
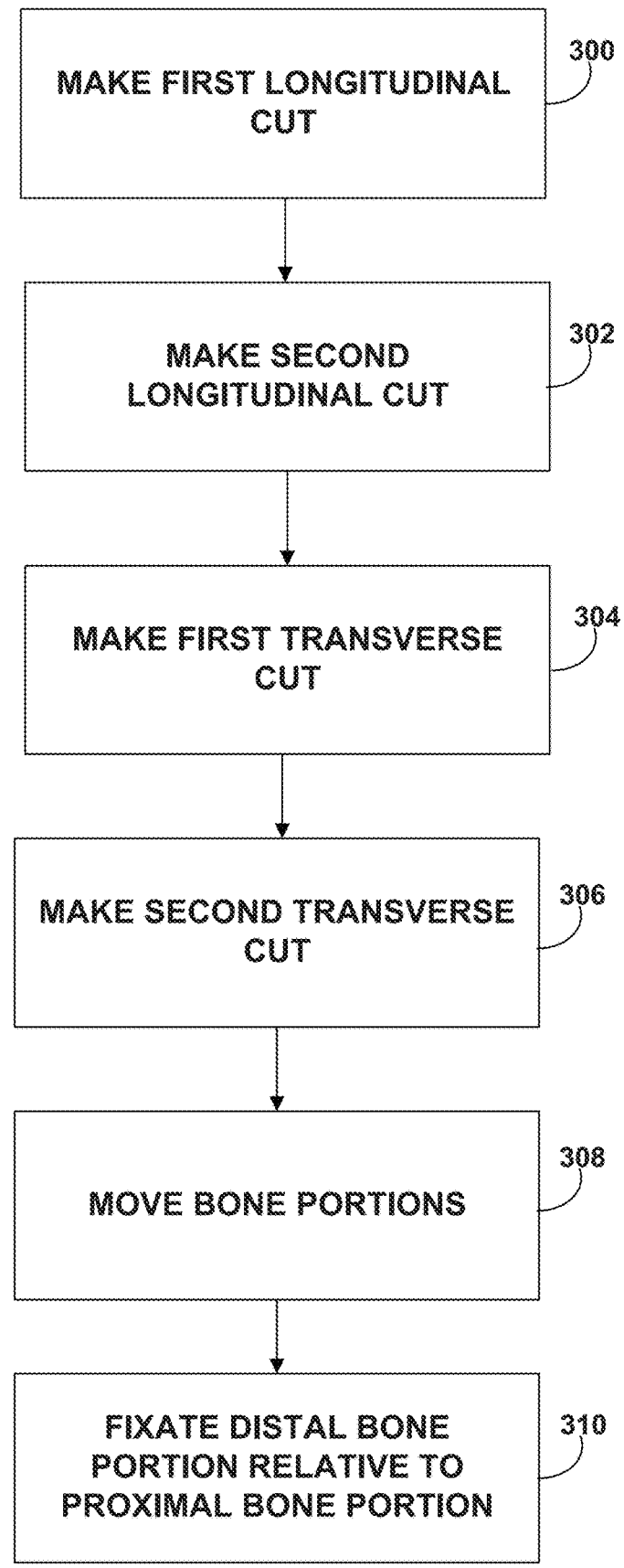
FIG. 4 is a flow diagram illustrating an example osteotomy technique for correcting an anatomical misalignment.
Figure 5B:
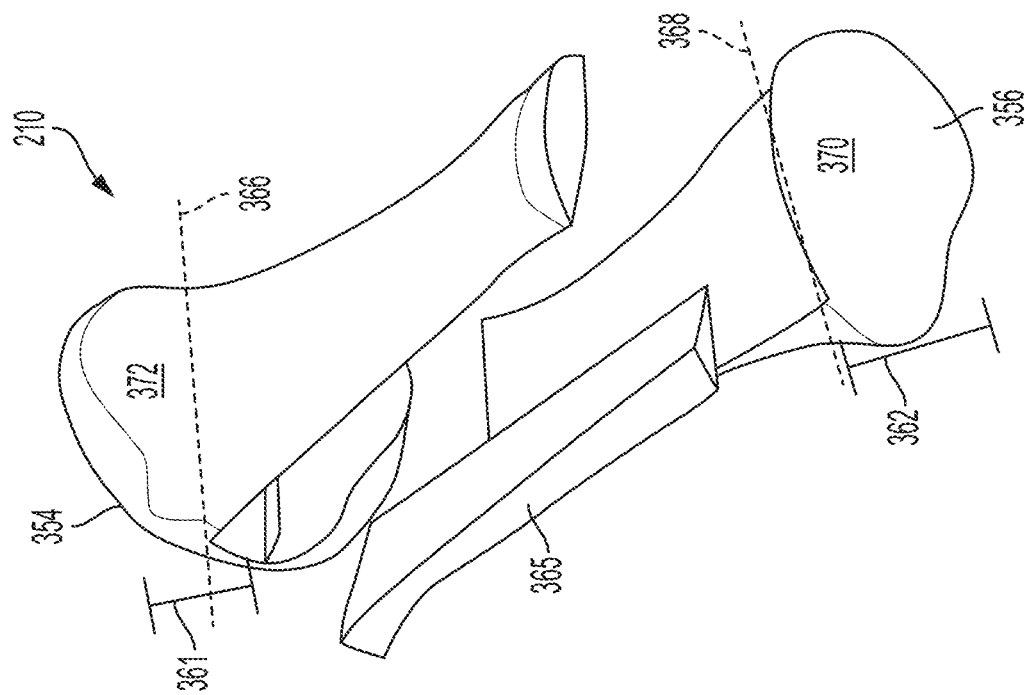
FIG. 5B is a perspective image of the example first metatarsal from FIG. 5A.
Figure 5A:
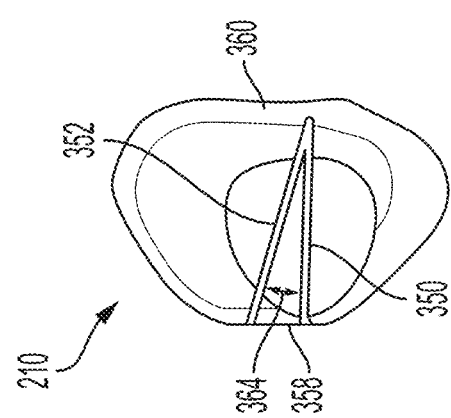
FIG. 5A is sectional image of a first metatarsal taken from the frontal plane showing example cut lines that can be made while performing the technique of FIG. 4.

FIG. 4 is a flow diagram illustrating an example osteotomy technique for correcting an anatomical alignment. The technique will be described with respect to first metatarsal 210 although can be performed on other bones, as discussed above. For purposes of discussion, the technique of FIG. 4 will be discussed with respect to two different images of first metatarsal 210 illustrated in FIGS. 5A and 5B to show how different cuts can be made along the first metatarsal during a bone correction procedure. FIG. 5A is sectional image of first metatarsal 210 from the frontal plane of the bone showing example cut lines that can be made while performing the technique of FIG. 4. FIG. 5B is a perspective image of first metatarsal 210 from FIG. 5A.

With reference to FIGS. 4 and 5, the example technique involves making a first longitudinal cut 350 into first metatarsal 210 (300) and also making a second longitudinal cut 352 into the first metatarsal that intersects the first longitudinal cut (302). The first longitudinal cut 350 may be made along the length of first metatarsal 210 between the proximal end 354 and distal end 356. In addition, the first longitudinal cut 350 may be made through the medial side 358 and the lateral side 360 of first metatarsal 210, thereby transecting the metatarsal along the lateral plane. In some examples, first longitudinal cut 350 is made from the medial side 358 of first metatarsal 210 toward the lateral side 360 of the metatarsal. The clinician may insert a cutting instrument from the medial side 358 of the bone and guide the cutting instrument towards the lateral side 360 of the bone to cut in this direction. Alternatively, the clinician may insert the cutting instrument from the lateral side 360 of the bone and guide the cutting instrument towards the medial side 358 of the bone. This alternative cutting direction may be useful when performing the procedure on, for example, the fifth metatarsal.

The clinician can make the first longitudinal cut 350 from the proximal end 354 of first metatarsal 210 toward the distal end 356 of the metatarsal. Alternatively, first longitudinal cut 350 can be made from the distal end 356 of the first metatarsal 210 toward the proximal end 354 of the bone. In some examples, first longitudinal cut 350 does not extend the entire length of first metatarsal 210 but instead extends only along a portion of the length of the metatarsal. For example, the proximal end of first longitudinal cut 350 may be offset from the proximal-most end 354 of first metatarsal 210 a separation distance 361. The distal end of first longitudinal cut 350 may also be offset from the distal-most end 356 of first metatarsal 210 a separation distance 362.

In some examples, separation distance 361 and separation distance 362 are substantially equal, e.g., such that first longitudinal cut 350 is substantially centered along the length of first metatarsal 210. In other examples, separation distance 361 and separation distance 362 are different from each other, e.g., such that first longitudinal cut 350 extends more proximately along the length of first metatarsal 210 then distally along the length. In some examples, first longitudinal cut 350 extends along at least 50% of the overall length of first metatarsal 210 between the proximal-most end 354 and the distal-most end 356 such as, e.g., at least 60% of the overall length, or from 50% to 80% of the overall length.

The technique of FIG. 4 also includes making second longitudinal cut 352 into first metatarsal 210 (302). The second longitudinal cut 352 may be made along the length of first metatarsal 210 between the proximal end 354 and the distal end 356. The second longitudinal cut 352 may extend the same length along first metatarsal 210 as first longitudinal cut 350 or may have a different length. Similarly, the second longitudinal cut 352 may be made from the medial side 358 of first metatarsal 210 or the lateral side 360 of the metatarsal, as discussed above with respect to the first longitudinal cut 350. In either case, the second longitudinal cut 352 may be made at a converging angle with respect to the first longitudinal cut 350 to form a wedge-shaped cut.

In the example of FIGS. 5A and 5B, second longitudinal cut 352 is shown as being radially offset from first longitudinal cut 350 (e.g., on the medial side 358 of first metatarsal 210) about an angle 364. In particular, in the illustrated example, first longitudinal cut 350 extends in a common transverse plane across first metatarsal 210 (in the medial to lateral direction) without angling in a plantar or dorsal direction across the bone. By contrast, second longitudinal cut 352 extends across first metatarsal 210 (in the medial to lateral direction) at an angle such that the medial end of second longitudinal cut 352 is positioned closer to the dorsal side of the metatarsal than the lateral side of the cut and, correspondingly, the lateral side of the cut is positioned closer to the plantar side of the metatarsal than the medial side of the cut. In the illustrated arrangement, second longitudinal cut 352 intersects first longitudinal cut 350 at the lateral side 360 of the first metatarsal 210, e.g., such that the apex of the resulting wedge is the lateral side of the bone. In other applications, second longitudinal cut 352 may not intersect first longitudinal cut 350 at the lateral side 360 of the first metatarsal 210 but may instead intersect the first longitudinal cut closer to the medial side 358 of the bone and/or may extend through the lateral side 360 of the first metatarsal without intersecting the first longitudinal cut.

Accordingly, in various applications, the first longitudinal cut 350 into first metatarsal 210 and/or the second longitudinal cut 352 into first metatarsal 210 may or may not extend all the way through the metatarsal (e.g., in the transverse plane). In FIGS. 5A and 5B, first longitudinal cut 350 and second longitudinal cut 352 are illustrated as both extending through first metatarsal 210 such that the cuts intersect at or outside of the lateral side 360 of first metatarsal 210. However, one of the cuts (e.g., which may be designated the first longitudinal cut) may extend through first metatarsal 210 while the other of the cuts extends into the first metatarsal and intersects the through cut within the cross-section of the bone. Thus, it should be appreciated that while first longitudinal cut 350 and second longitudinal cut 352 are illustrated as both extending through first metatarsal 210, one of the cuts may be an intersecting cut within the bone without extending through the entire cross-section of the bone.

In some examples, first longitudinal cut 350 is radially offset from second longitudinal cut 352 by an angle 364 ranging from 10° to 50°, such as from 15° to 35°. In addition, while FIG. 5A illustrates first longitudinal cut 350 extending across first metatarsal 210 in a single transverse plane and second longitudinal cut 352 extending across the first metatarsal at an angle in the dorsal to plantar direction from the medial to lateral side, it should be appreciated that one or both of the longitudinal cuts may be angled (e.g., in the plantar to dorsal direction) across one or more planes (e.g., moving proximally to distally along the first metatarsal and/or moving medially to laterally across the first metatarsal). Therefore, the example cut configuration of FIG. 5A is for purposes of illustration, and the disclosure is not limited in this respect.

To release the bone wedge formed by first longitudinal cut 350 and second longitudinal cut 352, the example technique of FIG. 4 also includes making a first transverse cut (304) and a second transverse cut (306). For example, FIG. 5B illustrates a bone wedge 365 formed by making a first transverse cut 366 and a second transverse cut 368. One or both of the first transverse cut 366 and the second transverse cut 368 may be made before or after making the first longitudinal cut 350 and/or making the second longitudinal cut 352. In general, the specific cutting order in which the first longitudinal cut 350, the second longitudinal cut 352, the first transverse cut 366, and the second transverse cut 368 are made can be rearranged at the discretion of the clinician performing the procedure.

The first transverse cut 366 may cut first metatarsal 210 in a frontal plane adjacent the proximal end 354 of the metatarsal. The second transverse cut 368 may cut first metatarsal 210 in a different frontal plane adjacent the distal end 356 of the metatarsal. In some examples, such as the example illustrated in FIG. 5B, the first transverse cut 366 extends downwardly, e.g., from a dorsal to plantar direction, from second longitudinal cut 352 and intersects both the first longitudinal cut 350 and the second longitudinal cut 352. Similarly, the second transverse cut 368 can extend upwardly, e.g., from a plantar to dorsal direction, from first longitudinal cut 350 and intersect both the first longitudinal cut 350 and the second longitudinal cut 352. This configuration of cuts can form a distal first metatarsal portion 370 whose length is defined by the dorsal portion of first metatarsal 210 and a proximal first metatarsal portion 372 whose length is defined by the proximal portion of the first metatarsal 210. Alternatively, the configuration of the first transverse cut 366 and the second transverse cut 368 can be reversed such that the first transverse cut extends upwardly from the first longitudinal cut 350 and the second transverse cut 368 extends downwardly from the second longitudinal cut 352. In this alternative configuration, the distal first metatarsal portion 370 can have a length defined by the plantar portion of the first metatarsal 210 while the proximal first metatarsal portion 372 can have a length defined by the dorsal portion of the metatarsal.

Independent of the direction in which the first transverse cut 366 and the second transverse cut 368 are made, one or both of the cuts may be within a single frontal plane or may be angled along the length of the first metatarsal across multiple frontal planes. For example, first transverse cut 366 may extend distally away from the end of second longitudinal cut 352. Second transverse cut 368 may also extend distally away from the end of the second longitudinal cut 352. This configuration of angled transverse cuts can provide a lock and key configuration, such as an interlocking "Z" shape, to help restrict relative movement between the distal first metatarsal portion 370 and the proximal first metatarsal portion 372 following realignment of the two bone portions. In alternative configurations, first transverse cut 366 may be angled proximally from the end of the second longitudinal cut 352, and second transverse cut 368 may be angled proximally from the end of the second longitudinal cut 352. In yet further configurations, the first transverse cut 366 or the second transverse cut 368 can be angled proximally while the other transverse cut is orthogonal or angled distally.

The example technique of FIG. 4 also involves moving the distal portion 370 of the first metatarsal 210 relative to the proximal portion 372 of the metatarsal in one or more planes to realign the distal portion of the bone relative the proximal portion (308). This can adjust the anatomical alignment of the distal portion 370 of the metatarsal relative to the proximal portion of the metatarsal, e.g., to help correct an anatomical misalignment. In some examples, the distal potion 370 of the first metatarsal 210 is rotated relative to the proximal portion 372 of the metatarsal. The distal portion 370 of the first metatarsal 210 may be rotated in the frontal plane and/or pivoted in the transverse plane and/or pivoted in the sagittal plane to help correct an anatomical misalignment of the distal portion 370. In some applications, the bone is pivoted by translating and/or sliding the bone. In some examples, the distal portion 370 of the first metatarsal 210 is rotated about an axis extending through the frontal plane so the medial side is moved dorsally and/or the distal portion 370 of the first metatarsal 210 is moved laterally in the transverse plane and/or plantarly in the sagittal plane. For example, the distal portion 370 of the first metatarsal 210 may be moved from an anatomically misaligned position relative to the proximal portion 372 of the first metatarsal and/or the second metatarsal 212 and/or the medial cuneiform 222 to an anatomically aligned position.

To facilitate movement of the distal portion 370 of the first metatarsal relative to the proximal portion 372 of the metatarsal, the wedge 365 formed by cutting the metatarsal can be removed from the space between the two bone portions. For example, the wedge-shaped bone portion 365 may be removed from between the two bone portions and the bone portions distracted or separated from each other to facilitate relative realignment. Alternatively, the wedge-shaped bone portion 365 may be removed from between the two bone portions and the bone portions realigned relative to each other without distracting the bone portions. In either case, the bone portions can shift and move relative to each other during realignment.

Figure 5C:
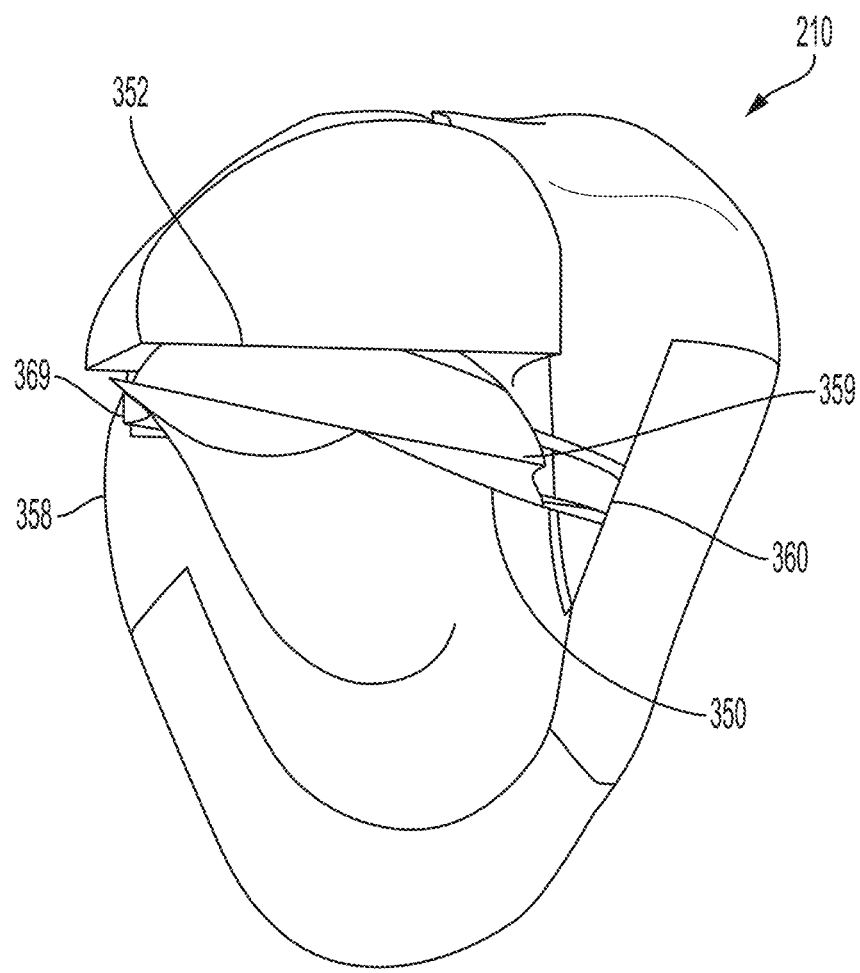
FIG. 5C is a sectional view of an example first metatarsal showing an example use of a wedge-shaped bone portion to close a gap created during realignment.
Figure 5D:
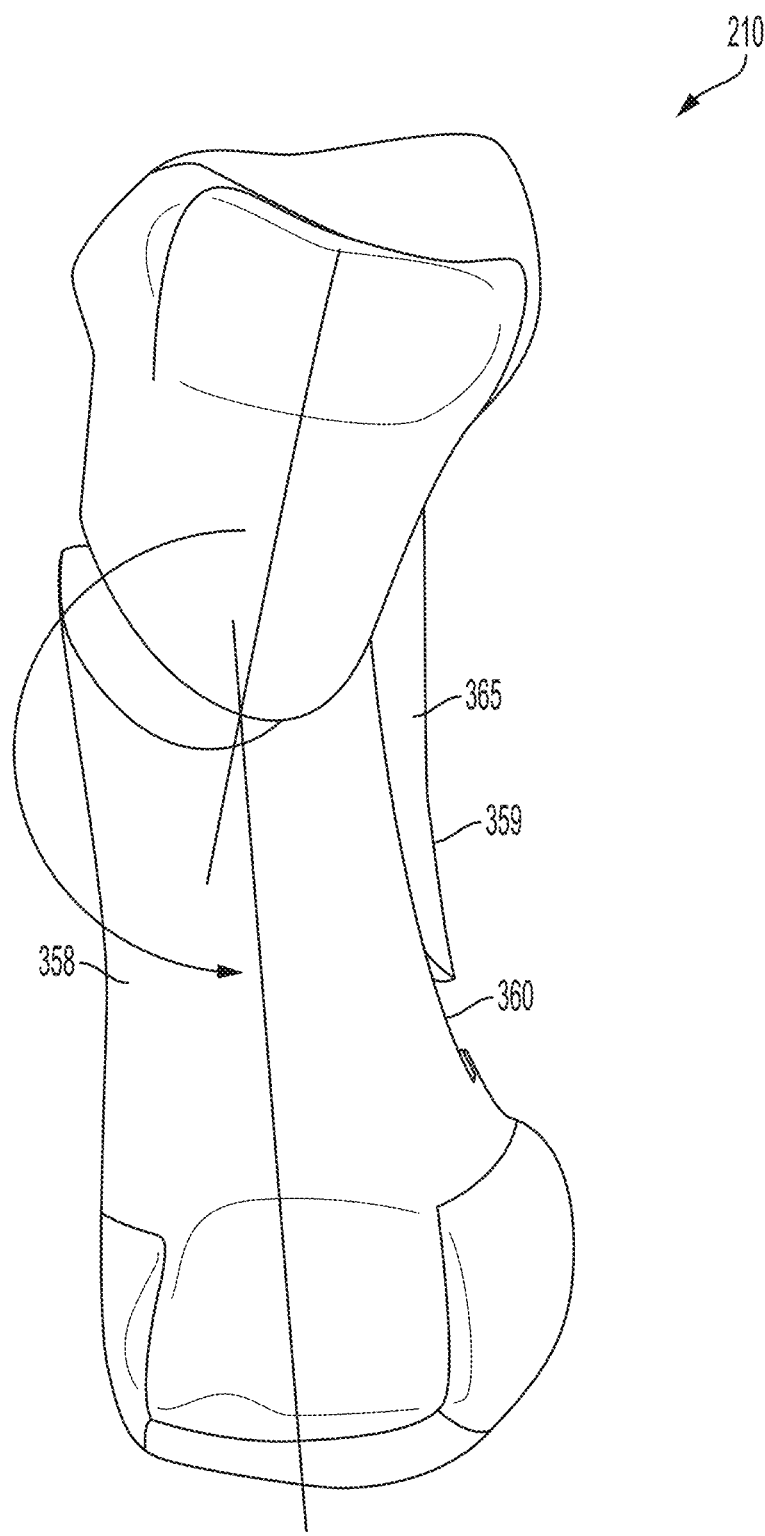
FIG. 5D is a dorsal perspective view of the example first metatarsal with wedge-shaped bone portion from FIG. 5C.

Wedge 365 removed from first metatarsal 210 may or may not be reused as an autograft to fill space created between distal portion 370 and proximal portion 372 of first metatarsal 210 during realignment. FIG. 5C is a sectional view of first metatarsal 210 from the frontal plane showing an example use of wedge-shaped bone portion 365 to close a gap created during realignment of distal portion 370 relative to proximal portion 372. FIG. 5D is a dorsal perspective view of the first metatarsal 210 with wedge-shaped bone portion 365 from FIG. 5C.

In the example shown in FIGS. 5C and 5D, wedge-shaped bone portion 365 has been removed from the medial side 350 of first metatarsal 210. This creates a wedge-shaped gap on the medial side between distal portion 370 and proximal portion 372. During subsequent realignment of distal portion 370 relative to proximal portion 372, the gap or void space created by removing wedge-shaped bone portion 365 can be closed. For example, as distal portion 370 is rotated in the frontal plane and/or translated in the transverse plane, the gap created by removing wedge-shaped bone portion 365 may be partially or fully closed. As the gap created by removing wedge-shaped bone portion 365 is closed, a second gap may be created on an opposite side of the first metatarsal. This gap or void space created by realignment of the two bone portions may be left open for self-healing or, as illustrated, a bone implant may be inserted into the gap to promote accelerated and efficacious recovery.

In some examples, wedge-shaped bone portion 365 defines a wedge extending from a base 359 to an apex 369. When resected from the medial side of first metatarsal 210, base 359 may be on the medial half of the medial half of the metatarsal while apex 369 is on the lateral half of the metatarsal. After being resected from first metatarsal, wedge-shaped bone portion 365 may be rotated 180 degrees (e.g., in the frontal plane and/or transverse plane) so apex 369 is oriented medially and base 359 is oriented laterally. The rotated wedge can then be inserted into the gap created through realignment between the distal portion 370 and proximal portion 372. The clinician may trim or otherwise resize the wedge-shaped bone portion 365 to be configured (e.g., sized and/or shaped) to fit within the opening created during realignment between the distal portion 370 and proximal portion 372. After trimming, the bone portion 365 inserted into the opening created by realignment between distal portion 370 and proximal portion 372 may or may not have a wedge shape (e.g., taping from a wider base to a narrower apex). It should be appreciated that the bone portion 365 may be inserted while the gap is opening and/or after distracting distal portion 370 and proximal portion 372. Accordingly, realignment between distal portion 370 and proximal portion 372 need not be performed or complete before inserting bone portion 365 on an opposite side of the metatarsal from which the bone portion was extracted.

The bone portion inserted in the opening created by realignment between distal portion 370 and proximal portion 372 may extend partially or fully across the cross-section of first metatarsal 210 in the transverse plane. In the example of FIG. 5C, bone portion 365 is illustrated as extending across the entire width of first metatarsal 210, e.g., such that the bone portion 365 is positioned between distal portion 370 and proximal portion 372 on both the medial side 350 of the metatarsal and the lateral side 360 of the metatarsal. However, bone portion 365 may be inserted only part way across the cross-section of first metatarsal 210, e.g., such that distal portion 370 and proximal portion 372 contact each other on the medial side 350 of the metatarsal.

When the wedge-shaped bone portion 365 resected from first metatarsal 210 is reused as a bone implant, the bone portion becomes an autograft within the surgical technique. Instead of reusing the bone portion harvested from the first metatarsal as an autograph, the clinician may use a different bone construct to fill the gap created through realignment, such as an allograft harvested from another person, a xenograft harvested from a different species, or synthetic bone.

After suitably moving the two transected bone portions relative to each other and, if desired, inserting a bone construct between the two bone portions, the bone portions (and optional inserted bone member) can be fixated to each other to secure and hold the new realigned position achieved through movement (310). In some examples, the distal and proximal bone portions (and optional inserted bone member) are provisionally fixated relative to each other before permanently fixating the bone portions relative to each other. Provisional fixation can temporarily hold the proximal bone portion 372 and distal bone portion 370 in fixed alignment relative to each other while one or more permanent fixation devices are applied to the bones and across the joints formed therebetween. A fixation wire and/or a compression pin, such as a threaded olive pin, may be used as provisional fixation instruments.

Independent of whether the distal bone portion 370 and proximal bone portion 372 are provisionally fixated together, the clinician may apply a permanent fixation device to the bone portions and across the joint between the bone portions (and optional inserted bone member). The permanent fixation device can hold the bone portions in fixed alignment relative to each other, e.g., to promote healing between the bone portions in their aligned positions. In different examples, one or more bone plates, pins, screws, staples, or other fixation mechanisms can be used to fixate the bones relative to each other.

In some examples, the clinician may resect bone around the perimeter of the cut end of the distal portion 370 of the first metatarsal and/or the proximal portion 372 of the first metatarsal. Rotating the distal portion 370 of the first metatarsal relative to the proximal portion 372 of the first metatarsal may cause the end of one of the bone portions to rotate out of plane, creating a projecting lip or edge. The clinician may use a cutting instrument to resect the lip or edge of the out-of-plane bone, helping to create a flush surface at the joint between the bone portions. The clinician may resect the protruding lip or edge of the cut end of the bone portion after moving the proximal and distal bone portions relative to each other. In different examples, the clinician can perform such resection before fixating the bone portions relative to each other or after fixating the bone portions relative to each other (e.g., either provisionally or permanently).

While the foregoing description of an example technique involves making a first longitudinal cut 350, a second longitudinal cut 352, a first transverse cut 366, and a second transverse cut 368, alternative implementations of the technique may be performed by making a lesser number of cuts.

As one example, first metatarsal 210 may be separated into a first portion and second portion by making two longitudinal cuts extending along the length of the metatarsal. The longitudinal cuts can extend along the length of the first metatarsal through the proximal end and distal end of the metatarsal. This can separate the first metatarsal 210 into two portions and release a removable bone wedge.

Figure 5E:
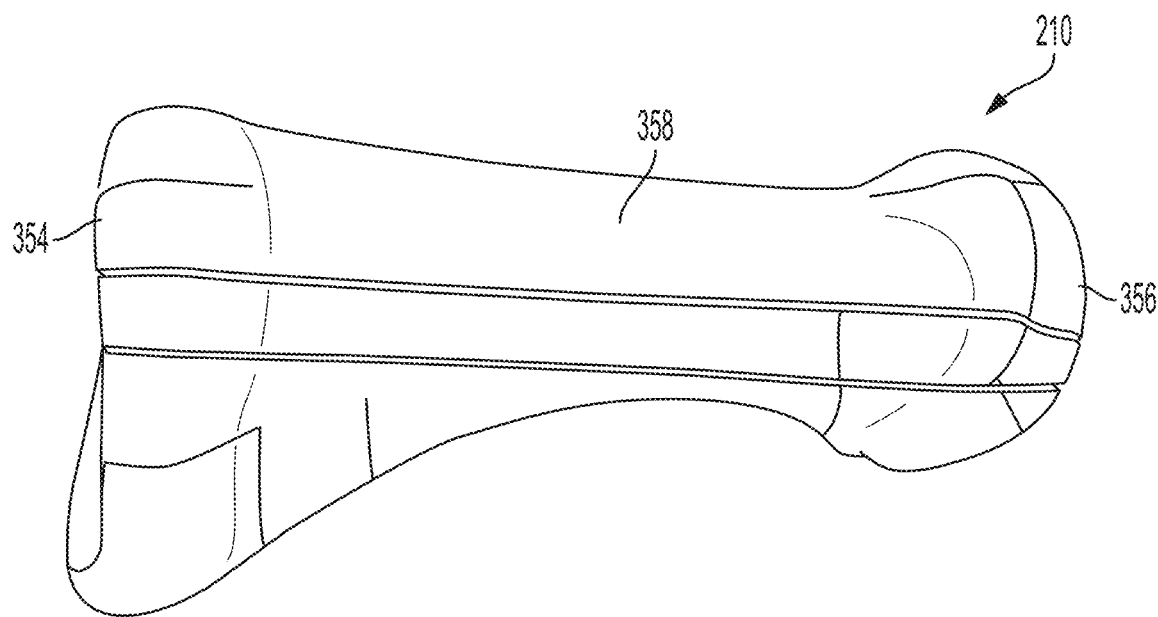
FIGS. 5E and 5F are a medial side view and a frontal plane view, respectively, of a first metatarsal illustrating an example technique in which the metatarsal is separated into two portions by making two cuts along the length of the metatarsal.
Figure 5F:
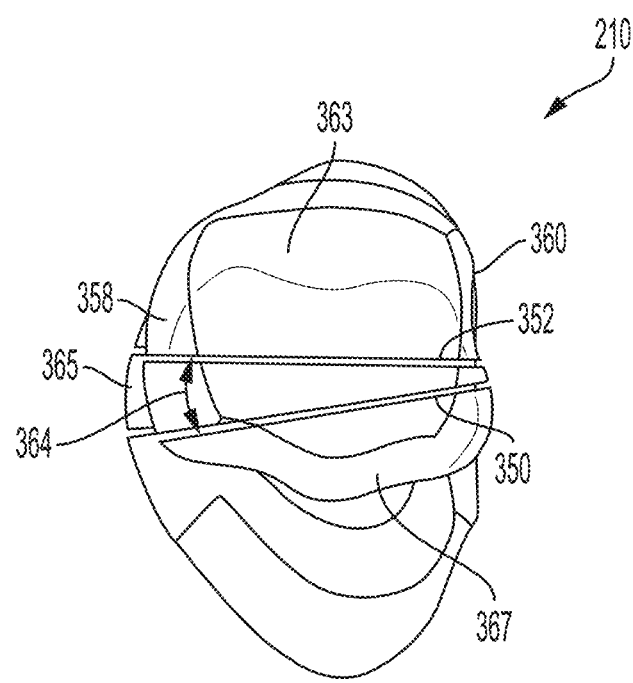

FIGS. 5E and 5F are a medial side view and a frontal plane view, respectively, of first metatarsal 210 illustrating an example technique in which the metatarsal is separated into two portions by making two cuts along the length of the metatarsal. As shown, first longitudinal cut 350 extends through the proximal end 354 and the distal end 356 of the first metatarsal 210 and also through the medial side 358 and lateral side 360 of the metatarsal. Second longitudinal cut 352 is radially offset from first longitudinal cut 350 (e.g., on the medial side 358 of first metatarsal 210) about angle 364. Second longitudinal cut 352 also extends through the proximal end 354 and the distal end 356 of the first metatarsal 210 as well as through the medial side 358 and lateral side 360 of the metatarsal.

The angle 364 of offset between first longitudinal cut 350 and second longitudinal cut 352 may be within the ranges discussed above with respect to FIGS. 5A and 5B. For example, first longitudinal cut 350 may be radially offset from second longitudinal cut 352 by an angle 364 ranging from 10° to 50°, such as from 15° to 35°. In addition, in the illustrated example, first longitudinal cut 350 and second longitudinal cut 352 each extend transversely across first metatarsal 210 (in the medial to lateral direction) without angling in a plantar or dorsal direction across the bone. However, one or both of the longitudinal cuts may angle, e.g., in a planar to dorsal direction or vice versa across the length of the bone, as discussed above.

In practice, a clinician can use a cutting instrument to cut first metatarsal 210 along first longitudinal cut 350 and second longitudinal cut 352. This can separate the first metatarsal into a first portion 363, a second portion 367, and wedge-shaped bone portion 365. The wedge-shaped bone portion 365 formed by cutting the metatarsal can be removed from the space between the two bone portions. For example, the wedge-shaped bone portion 365 may be removed from between the two bone portions and the bone portions distracted or separated from each other to facilitate relative realignment. Alternatively, the wedge-shaped bone portion 365 may be removed from between the two bone portions and the bone portions realigned relative to each other without distracting the bone portions. In either execution, the bone portions can be realigned relative to each other, as discussed above.

Figure 5G:
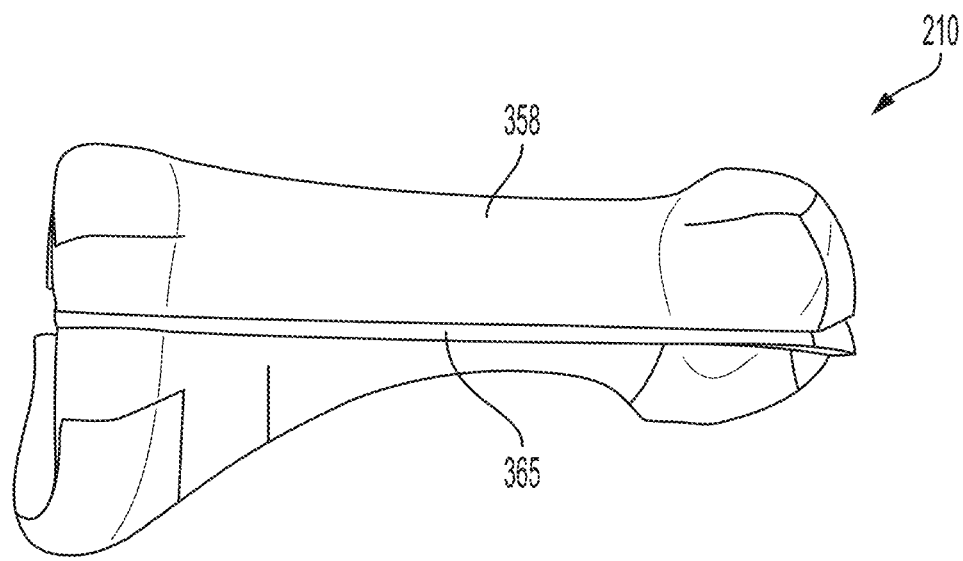
FIGS. 5H and 5G are a medial side view and a frontal plane view, respectively, showing an example use of wedge-shaped bone portion in a metatarsal realignment technique.
Figure 5H:
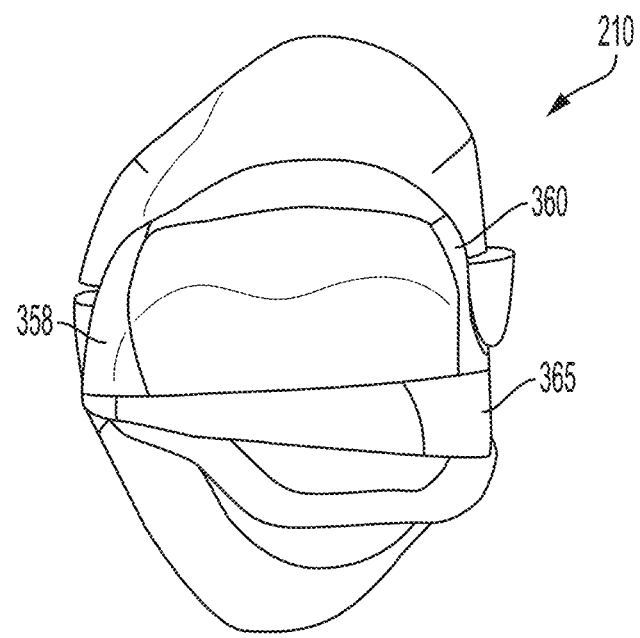

In some examples, the wedge-shaped bone portion 365 removed from between the first bone portion 363 and the second bone portion 367 is used as a bone implant in a gap during realignment of the first bone portion 363 relative to the second bone portion 367. For example, as discussed with respect to FIGS. 5C and 5D, a gap created by removing wedge-shaped bone portion 365 may be closed while realigning the first bone portion 363 relative to the second bone portion 367. As this gap is closed, a second gap may be created on an opposite side of the first metatarsal. The wedge-shaped bone portion 365 resected from first metatarsal 210 can be reused as a bone implant in this second gap. For example, FIGS. 5H and 5G are a medial side view and a frontal plane view, respectively, showing an example use of wedge-shaped bone portion 365 in a metatarsal realignment technique. As discussed above with respect to FIGS. 5C and 5D, wedge-shaped bone portion 365 may be rotated 180 degrees (e.g., in the frontal plane and/or transverse plane) and inserted into the gap created through realignment between the first bone portion 363 and the second bone portion 367. Instead of reusing the bone portion harvested from the first metatarsal as an autograph in the technique of FIGS. 5E and 5H, the clinician may use a different bone construct to fill the gap created through realignment, such as an allograft harvested from another person, a xenograft harvested from a different species, or synthetic bone.

After suitably moving the two bone portions relative to each other and, if desired, inserting a bone construct between the two bone portions, the bone portions (and optional inserted bone member) can be fixated to each other to secure and hold the new realigned position achieved through movement. In some examples, the bone portions (and optional inserted bone member) are provisionally fixated relative followed by permanent fixation.

Figure 6A:
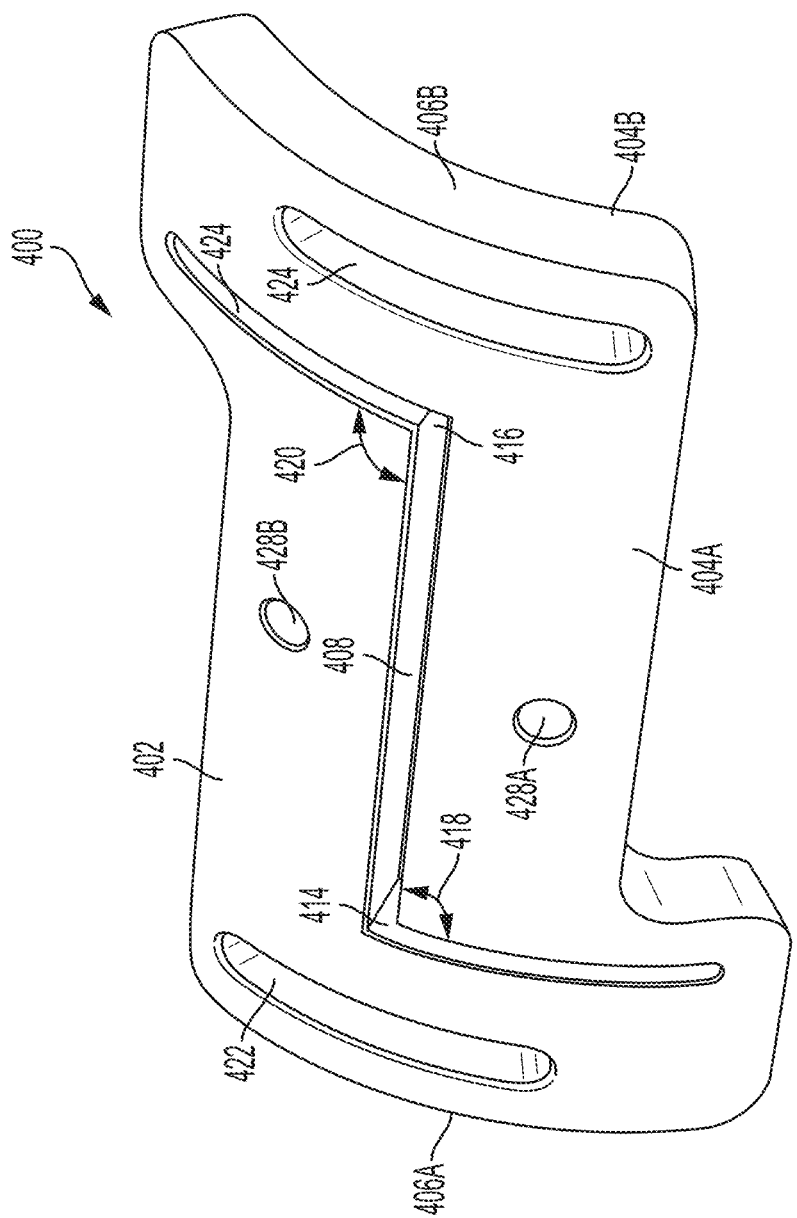
FIG. 6A is a perspective view of one example cutting guide that can be used to cut a first metatarsal to realign a distal portion of the metatarsal relative to a proximal portion of the metatarsal.

A variety of different cutting instruments and cutting guides can be used to implement the technique discussed above with respect to FIGS. 4 and 5. FIG. 6A is a perspective view of one example cutting guide 400 that can be used to cut a first metatarsal 210 to realign a distal portion 370 of the metatarsal relative to a proximal portion 372. As shown in the illustrated example of FIG. 6A, cutting guide may be defined by a body 402 that is configured (e.g., sized and/or shaped) to be positioned against a bone to be cut. For example, body 402 may define a front side 404A and a backside 404B that is opposite the front side. Body 402 may further extend from a first longitudinal side edge 406A to a second longitudinal side edge 406B. In use, body 402 may be positioned against a first metatarsal to be cut such that backside 404B is in contact with the metatarsal while the front side 404A faces outwardly away from the metatarsal. When so positioned, first longitudinal side edge 406A can be positioned closer to the proximal end of the first metatarsal from the distal end, while second longitudinal side edge 406B can be positioned closer to the distal end of the first metatarsal and the proximal end.

Body 402 of cutting guide 400 may have a variety of different shapes. In some examples, body 402 is shaped to conform to the curvature of a bone to be cut. For example, body 402 may have a "V" shape or a radius of curvature that conforms to the radius of curvature of a bone to be cut. When so configured, body 402 may wrap at least partially about the curved external surface of the bone to be cut.

To cut a first metatarsal along the length of the bone, cutting guide 400 can have at least one longitudinal cutting slot 408. The longitudinal cutting slot 408 may extend at least partially, and in some examples fully, along the length of the cutting guide body 402 between the first longitudinal side edge 406A and the second longitudinal side edge 406B. The longitudinal cutting slot 408 may extend across body 402 at a constant vertical location on the body (e.g., as illustrated in FIG. 6A) or may slope upwardly or downwardly across the length of the body.

To create transverse cuts on the first metatarsal, cutting guide 400 may further include at least one transverse cutting slot which, in the example of FIG. 6A, is illustrated as two transverse cutting slots: first transverse cutting slot 410 and second transverse cutting slot 412. First transverse cutting slot 410 may extend downwardly from the longitudinal cutting slot 408, and the second transverse cutting slot 412 may extend upwardly from the longitudinal cutting slot. For example, longitudinal cutting slot 408 may run from a first terminal end 414 to a second terminal end 416. First transverse cutting slot 410 can extend downwardly from the first terminal end 414 of the longitudinal cutting slot, e.g., such that the first transverse cutting slot and the longitudinal cutting slot share a common terminal end 414. Second transverse cutting slot 412 can extend upwardly from the second terminal end 416 of the longitudinal cutting slot, e.g., such that the second transverse cutting slot in longitudinal should cutting slot share a common terminal end 416.

The first transverse cutting slot 410 can intersect the longitudinal cutting slot 408 at a first intersection angle 418. The second transverse cutting slot 412 can intersect the longitudinal cutting slot 408 at a second intersection angle 420. In the illustrated example, the first and second intersection angles 418, 420 are illustrated as being approximately orthogonal or 90°. In different examples, the first and second intersection angles 418, 420 may range from 20° to 135°, such as less than 90°, from 20° to 80°, from 30° to 75°, or yet other angles. In some examples, the first and second intersection angles 418, 420 may be offset from orthogonal from 1° to 45°. The first and second intersection angles 418, 420 may be the same or may be different from each other.

In some examples, first transverse cutting slot 410 is sloped proximately moving away from longitudinal cutting slot 408. For example, when cutting guide 400 is applied to a first metatarsal, terminal end 414 of the first transverse cutting slot may be positioned more distally along the length of the bone then the opposite end of the cutting slot. Where second transverse cutting slot 412 is sloped at a corresponding angle, terminal end 416 of the second transverse cutting slot may be positioned more proximately along the length of the bone than the opposite end of the cutting slot.

Bone cutting guide 400 can have any suitable dimensions. In some examples, longitudinal cutting slot 408, first transverse cutting slot 410, and second transverse cutting slot 412 each have a width ranging from 0.1 mm to 3 mm. The dimensions of each of the different cutting slots may be the same or may be different from each other. For example, the dimensions of each of the cutting slots may be the same and may be sized based on the particular cutting instrument (e.g., saw blade, rotary bur, osteotome) intended to be used for the surgical procedure. Longitudinal cutting slot 408, first transverse cutting slot 410, and/or second transverse cutting slot 412 may extend perpendicularly through the thickness of body 402 or may be angled as the slot extends through the thickness of the body, e.g., to provide an angled cutting slot.

To attach bone cutting guide 400 to a bone to be cut during a surgical procedure, body 402 may include one or more fixation apertures configured to receive a fixation member, such as a wire, pin, screw, or other mechanical fixation element intended to temporarily secure and hold the cutting guide to the bone during the surgical procedure. In the example of FIG. 6A, body 402 includes a first slot 422 and a second slot 424 that function as fixation apertures. First slot 422 is positioned between the first longitudinal edge 406A of body 402 and first transverse cutting slot 410. Second slot 424 is positioned between the second longitudinal side edge 406B of body 402 and second transverse cutting slot 412. First slot 422 and second slot 424 are illustrated as being parallel to first transverse cutting slot 410 and second transverse cutting slot 412, respectively, but may not be parallel in other configurations. In general, slots 422 and 424 may be sufficiently long to allow cutting guide 400 to be positioned at different radial or angular locations about the first metatarsal 210 being cut, e.g., to allow different cuts at different radial or angular positions along the bone to be made using longitudinal cutting slot 408.

Figure 6B:
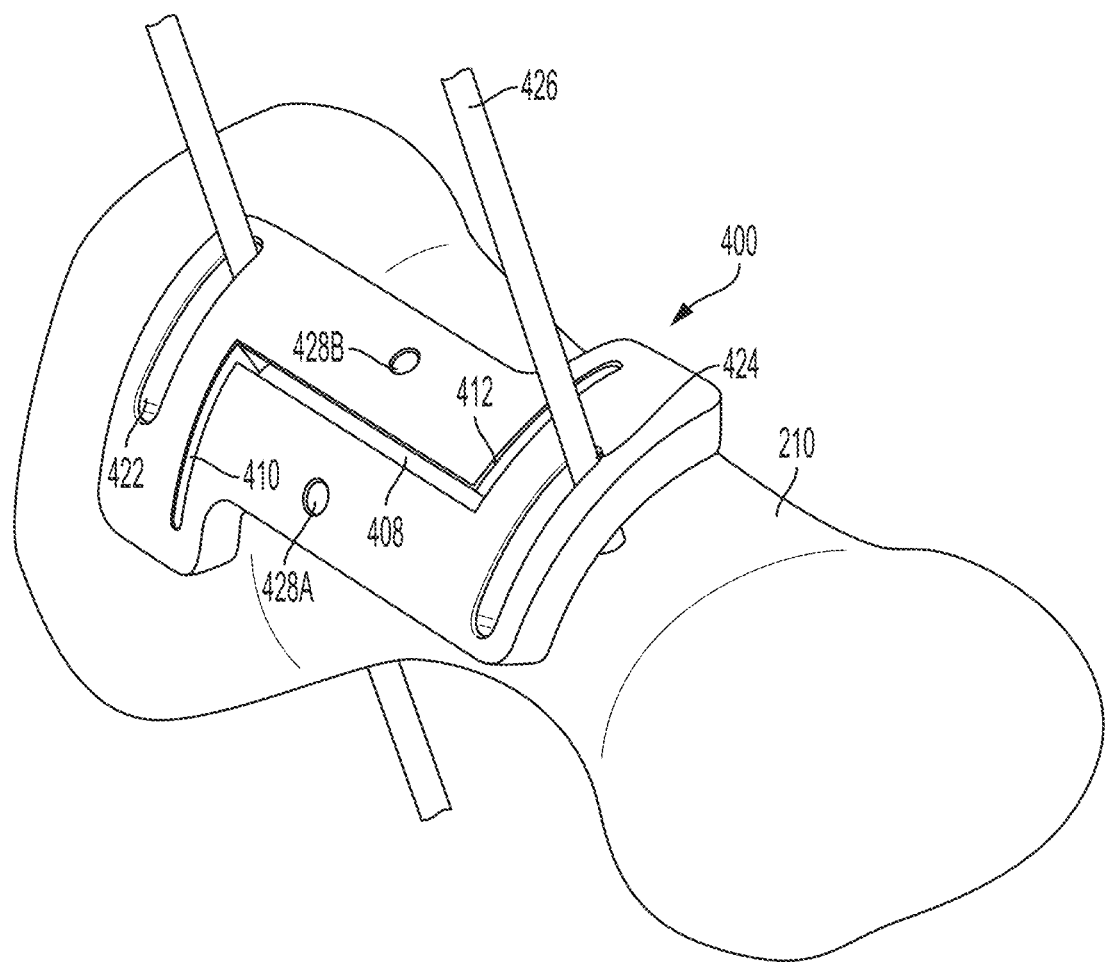
FIG. 6B is a perspective view of the example cutting guide of FIG. 6A shown attached to a first metatarsal.

FIG. 6B is a perspective view of cutting guide 400 attached to a first metatarsal 210 using slots 422 and 424. As shown in this example, fixation pins 426 are inserted through each of slots 422 and 424 to position bone cutting guide 400 at a first radial position on the first metatarsal. Bone cutting guide 400 can be rotated radially about first metatarsal 210 to a second radial position while fixation pins 426 remain in slots 422 and 424, e.g., to reposition the location of longitudinal cutting slot 408. This can be useful to position bone cutting guide 400 at one location to make first longitudinal cut 350 (FIG. 5A) and subsequently rotate the cutting guide to a second location to make second longitudinal cut 352. Bone cutting guide 400 may include one or more additional fixation apertures 428A, 428B to secure the bone cutting guide at a particular rotational orientation about first metatarsal 210.

Figure 7A:
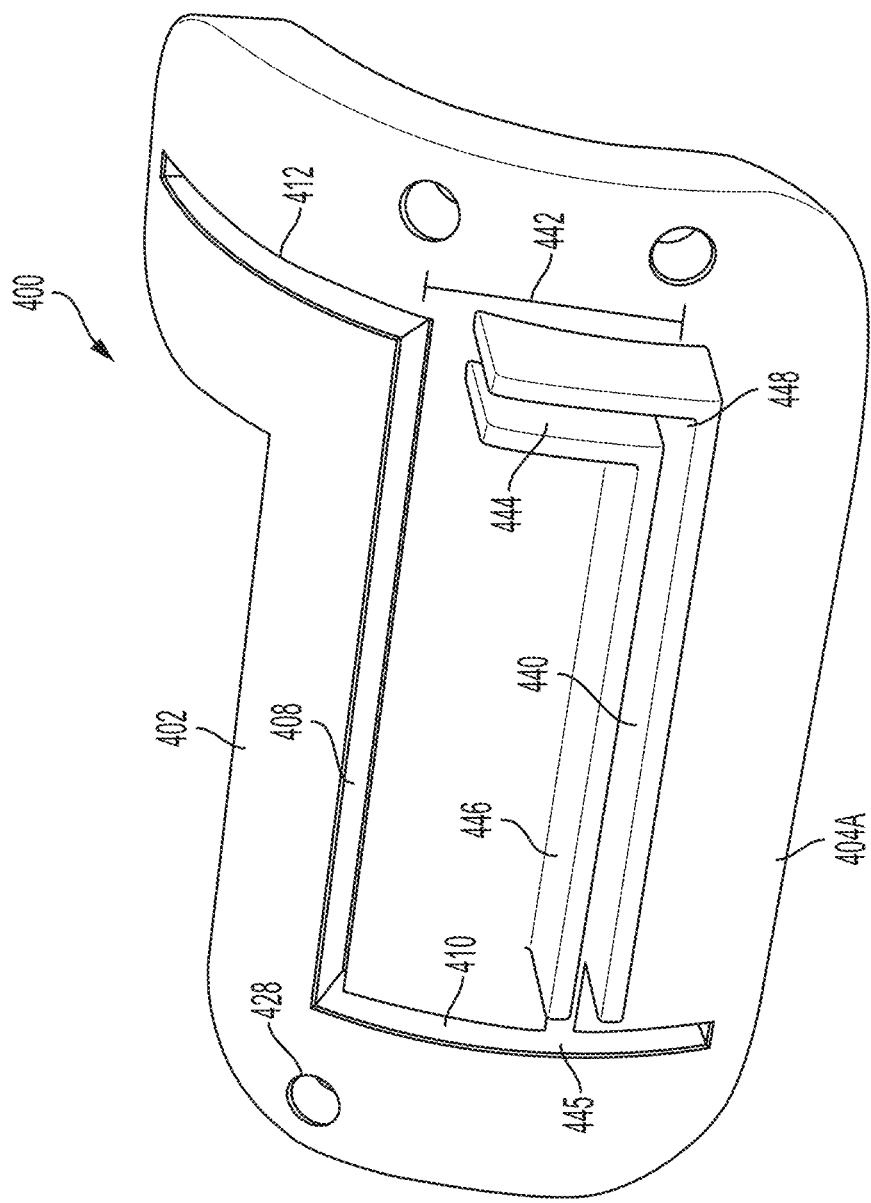
FIG. 7A is a perspective illustration of another example configuration of a bone cutting guide that can be used to cut a first metatarsal to realign a distal portion of the metatarsal relative to a proximal portion of the metatarsal.

FIG. 7A is a perspective illustration of another example configuration of bone cutting guide 400 where like features discussed above with respect to FIGS. 6A and 6B refer to like elements. As shown in this example, bone cutting guide 400 includes the previously described longitudinal cutting slot 408, first transverse cutting slot 410, and second transverse cutting slot 412. In addition, in the example configuration of FIG. 7A, bone cutting guide 400 includes a second longitudinal cutting slot 440. Second longitudinal cutting slot 440 may extend parallel to the first longitudinal cutting slot 408 and may be offset relative to the first longitudinal cutting slot. For example, the first longitudinal cutting slot 408 and the second longitudinal cutting slot 440 may be offset from their centerlines a distance 442 ranging from 2 mm to 35 mm, such as from 5 mm to 20 mm.

Second longitudinal cutting slot 440 can extend parallel to first longitudinal cutting slot 408 and intersect first transverse cutting slot 410. For example, second longitudinal cutting slot 440 may intersect first transverse cutting slot 410 at a location between the terminal ends of the transverse cutting slot. In use, a clinician may use first longitudinal cutting slot 408 and second longitudinal cutting slot 440 to make the two longitudinal cuts along the length of first metatarsal 210 discussed above with respect to FIGS. 4 and 5. In such applications, first longitudinal cutting slot 408 and second longitudinal cutting slot 440 may be angled relative to each other to form converging cut lines that intersect on first metatarsal 210. For example, first longitudinal cutting slot 408 and second longitudinal cutting slot 440 may be angled relative to each other to form cutting lines that converge at an angle ranging from 5° to 45°.

To help form second transverse cut 368 (FIG. 5B), cutting guide 400 in FIG. 7A may include a third transverse cutting slot 444 that is co-linear with a second transverse cutting slot 412. For example, second longitudinal cutting slot 440 may extend from a first end 445 to a second end 448. The first end 445 of the second longitudinal cutting slot 440 can intersect first transverse cutting slot 410. Third transverse cutting slot 444 can extend upwardly from the second end 448 of the second longitudinal cutting slot 440. In practice, a clinician may insert a cutting instrument through both second transverse cutting slot 412 and third transverse cutting slot 444 to form a joined, single transverse cut line 368 (FIG. 5B) to help separate a distal metatarsal portion 370 from a proximal metatarsal portion 372.

To help control the depth of cut being made by a clinician using bone cutting guide 400, the cutting guide may include a depth limiter. The depth limiter may be a surface against which the clinician can position a cutting instrument and along which the clinician can translate the cutting instrument through a cutting slot in order to set the depth of cut made through the slot. The depth limiter may be permanently joined/integrally formed with the body 402 or may be a separate component attachable to or used in conjunction with body 402.

In the example of FIG. 7A, bone cutting guide 400 includes a depth limiter 446, which is defined by a surface projecting outwardly from the first side 404A of body 402. In particular, in the illustrated configuration, depth limiter 446 includes one surface or rail projecting outwardly from body 402 on one side of second longitudinal cutting slot 440 and a second surface or rail projecting outwardly from the body on an opposite side of the longitudinal cutting slot. In some examples, depth limiter 446 projects outwardly from the first side 404A of body 402 a distance ranging from 0.25 mm to 10 mm. A clinician may place their cutting instrument against depth limiter 446, e.g., with a cutting blade or member inserted through the slot, and guide the cutting instrument along the depth limiter to form a cut of controlled depth.

Figure 7B:
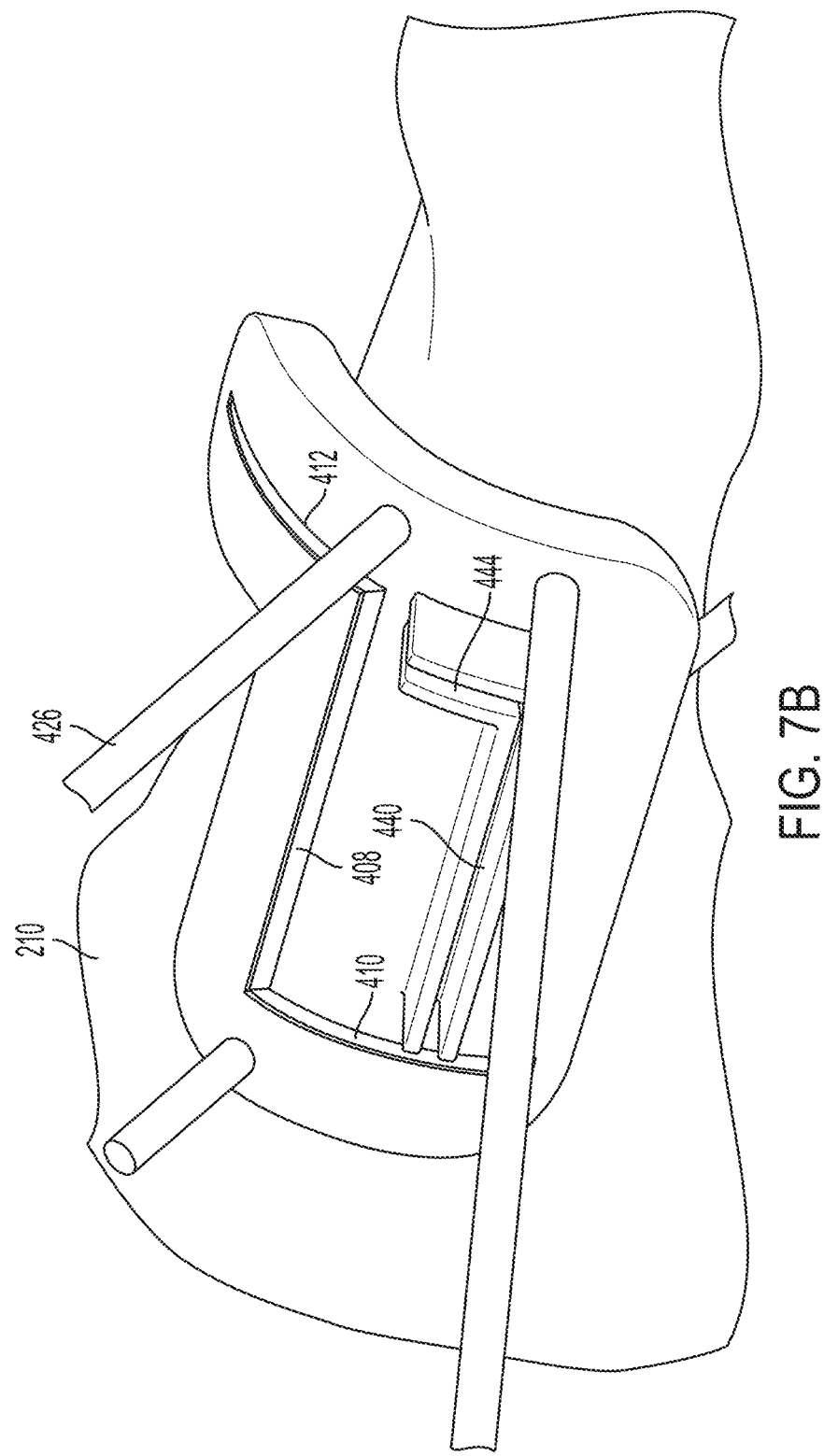
FIG. 7B is a perspective illustration of the example cutting guide of FIG. 7A shown attached to a first metatarsal.

As discussed above with respect to the example configuration of bone cutting guide 400 in FIGS. 6A and 6B, bone cutting guide 400 in the example of FIG. 7 may include one or more fixation apertures to temporarily fixate the bone cutting guide against a bone to be cut during a procedure. In the illustrated configuration, bone cutting guide 400 includes three fixation apertures 428, although a different number of fixation apertures may be used. FIG. 7B is a perspective illustration of bone cutting guide 400 from FIG. 7A showing the cutting guide attached to an example first metatarsal 210.

Figure 8:
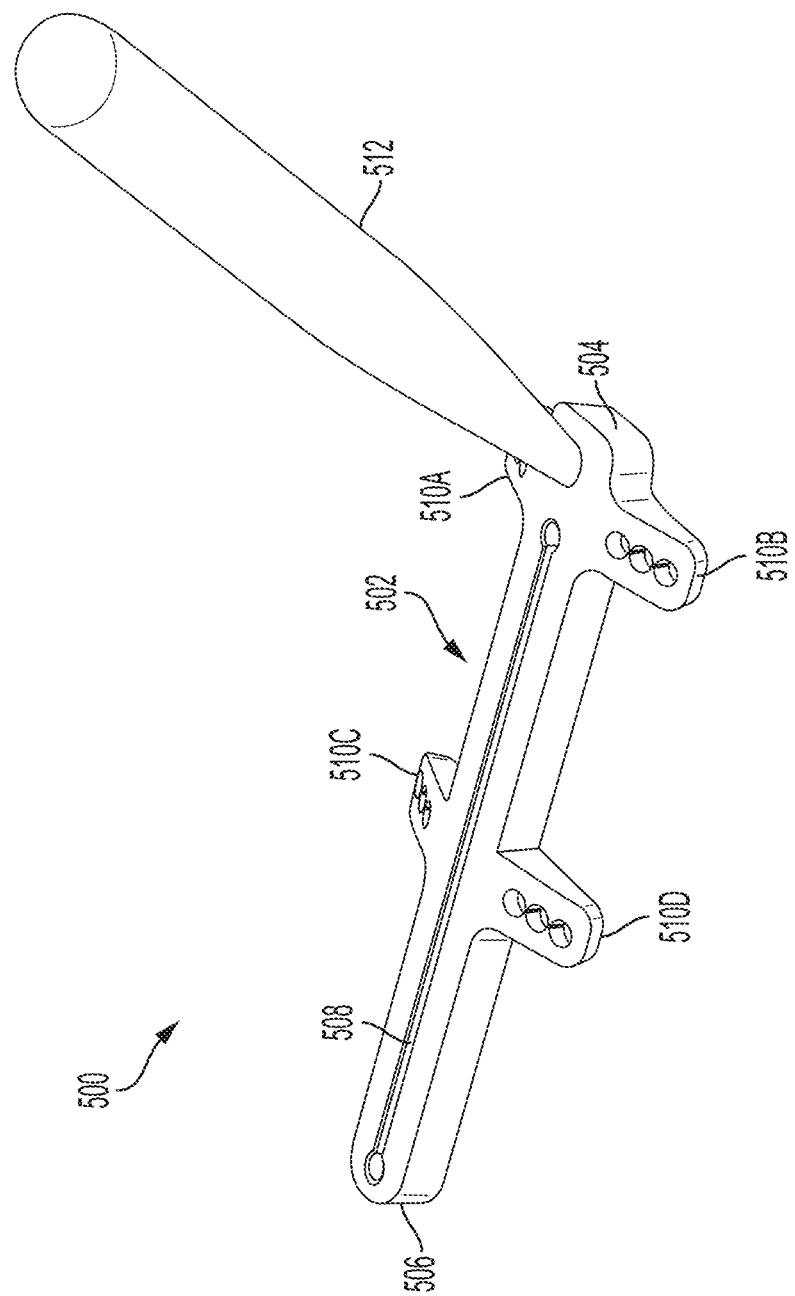
FIG. 8 is a perspective illustration of another example bone cutting guide that can be used according to the disclosure.
Figure 9A:
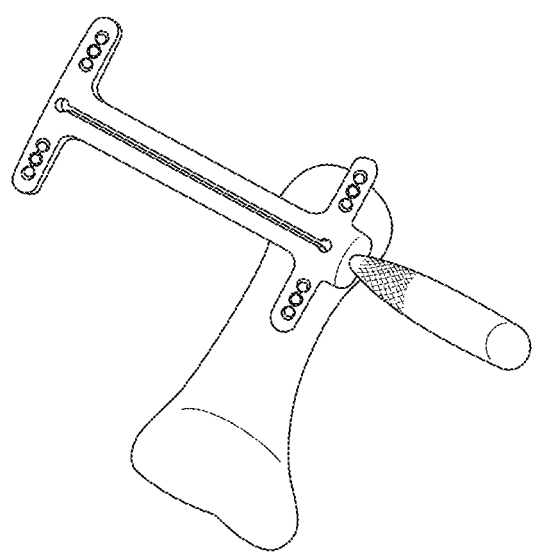
FIGS. 9A-9D are conceptual illustrations showing how the example bone cutting guide of FIG. 8 can be manipulated relative to a bone to be cut to execute a bone realignment technique.
Figure 9B:
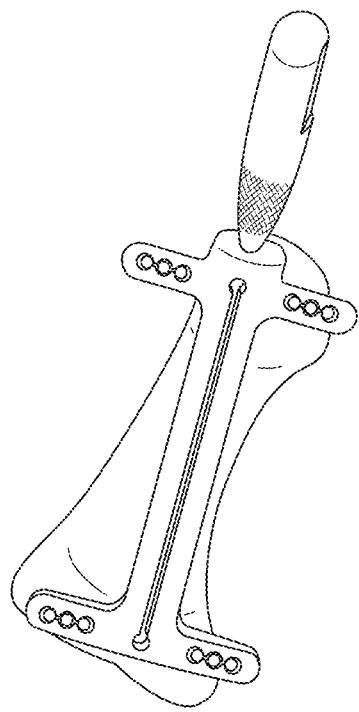
Figure 9C:
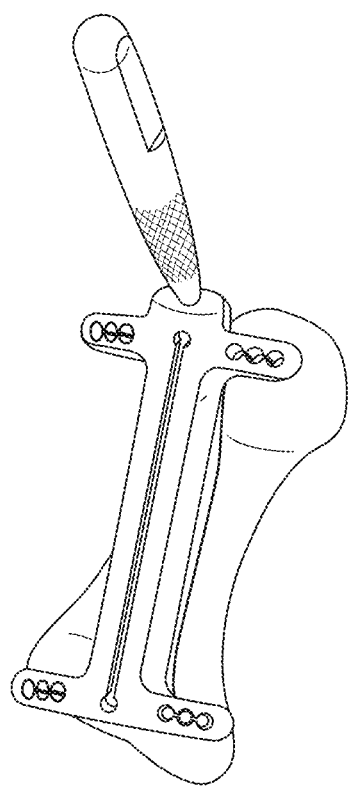
Figure 9D:
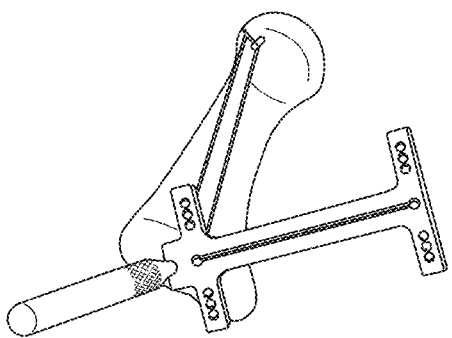

As mentioned, a variety of different cutting guide configurations can be used during a bone realignment procedure according to the present disclosure. FIG. 8 is a perspective illustration of another example bone cutting guide 500 that can be used according to the disclosure. As shown in this example, bone cutting guide 500 has a body 502 that extends from a first end 504 to a second end 506. A longitudinal cutting slot 508 is formed through the body 502 and extends along the length of the body between the first end 504 and the second end 506. A clinician may manipulate cutting guide 500 to position longitudinal cutting slot 508 at different positions along a first metatarsal 210 to be cut.

To temporarily secure cutting guide 500 at one or more different positions against the bone to be cut, the cutting guide may include securing projections. For example, cutting guide 500 may include a first securing projection 510A and a second securing projection 510B extending substantially orthogonally (or at a different angle) relative to the length of the body. Each securing projection can have at least one, and in some examples multiple, fixation apertures configured to receive a mechanical fixation element for securing the body to a bone to be cut. For example, each securing projection may include multiple fixation apertures that are linearly aligned (e.g., in an orthogonal direction away from the length of the body). The different securing projections may allow bone cutting guide 500 to be positioned at different degrees of rotation about the bone to be cut, e.g., by selecting different rotational positions corresponding to different sets of fixation apertures.

In different examples, bone cutting guide 500 may include more than two securing projections, such as three, four or more securing projections. In the illustrated configuration, bone cutting guide 500 includes four securing projections 510A-510D. First and second securing projections 510A and 510B may be located adjacent the first end 504 of body 502, while the third and fourth securing projections 510C and 510D may be located adjacent the second end 506 of the body.

To manipulate bone cutting guide 500 during use, the bone cutting guide may include a handle 512. The handle may extend from the body 502 and angle ranging from 10° to 90°. The handle can be permanently attached to body 502 or can be removably coupled to the body, e.g., threadingly coupled to the body. In some applications, a clinician may hold bone cutting guide 500 against a bone to be cut while performing a cutting operation without securing the cutting guide to the bone with a mechanical fixation instrument using a securing projection. In other applications, the clinician may manipulate bone cutting guide 500 against the bone using handle 512 but may provisionally fixate the bone cutting guide against the bone using a mechanical fixation element inserted through one or more securing projections before performing a cutting procedure. FIGS. 9A-9D are conceptual illustrations showing how bone cutting guide 500 can be manipulated relative to a bone to be cut to execute a bone realignment technique as discussed herein.

In the foregoing description, certain features, elements, and techniques have been described with respect to relative references such as "upwardly" and "downwardly." It should be appreciated that such relative references are used for purposes of illustration based on the orientation in the figures. More generally, the features, elements, and techniques may change orientation in three-dimensional space. Accordingly, references to "upwardly" and "downwardly" should be considered relative and not confined to a specific orientation with respect to gravity.

Various examples have been described. These and other examples are within the scope of the following claims.

The invention claimed is:

1. A method of correcting a bunion, the method comprising:
   positioning a cutting guide against a medial side of a first metatarsal, the cutting guide having a body defining a backside positioned against the first metatarsal, a frontside positioned facing away from the first metatarsal, a first side edge, and a second side edge, the second side edge being positioned closer to the distal end of the first metatarsal than the first side edge, wherein the cutting guide comprises an angled cutting slot having a first terminal end and a second terminal end with the first terminal end positioned more distally along a length of the first metatarsal than the second terminal end;
   guiding a cutting instrument through the angled cutting slot to cut the first metatarsal into a distal metatarsal portion and a proximal metatarsal portion;
   moving the distal metatarsal portion relative to the proximal metatarsal portion in a transverse plane and in a frontal plane to correct a bunion misalignment of the first metatarsal;
   applying provisional fixation to temporarily hold the distal metatarsal bone portion in a fixated alignment relative to the proximal metatarsal bone portion; and
   applying permanent fixation to hold the distal metatarsal bone portion in a fixated alignment relative to the proximal metatarsal bone portion.

2. The method of claim 1, wherein moving the distal metatarsal portion in the frontal plane comprises rotating the distal metatarsal portion until a tibial sesamoid bone and a fibular sesamoid bone are on opposite sides of a sagittal plane when viewed from the frontal plane.

3. The method of claim 1, wherein moving the distal metatarsal portion in the transverse plane comprises reducing an intermetatarsal angle between the distal metatarsal portion and a second metatarsal to 10 degrees or less.

4. The method of claim 1, wherein moving the distal metatarsal portion in the transverse plane comprises reducing an intermetatarsal angle between the distal metatarsal portion and a second metatarsal to within 1 to 5 degrees.

5. The method of claim 1, wherein guiding the cutting instrument through the angled cutting slot to cut the first metatarsal comprises cutting the first metatarsal at a proximal portion of the first metatarsal.

6. The method of claim 1, wherein the cutting guide comprises fixation apertures, and further comprising, prior to cutting the first metatarsal, attaching the cutting guide to the first metatarsal proximally and distally of a location where the first metatarsal is to be cut.

7. The method of claim 6, wherein the fixation apertures comprises slots.

8. The method of claim 1, wherein applying permanent fixation comprises applying one or more of a bone plate, pin, screw, and staple.

9. The method of claim 1, wherein applying permanent fixation comprises applying a bone plate and screws.

10. The method of claim 1, wherein applying permanent fixation comprises applying one or more staples.

11. The method of claim 1, wherein applying provisional fixation comprises applying a fixation wire and/or a compression pin between the proximal metatarsal portion and the distal metatarsal portion.

12. The method of claim 1, wherein guiding the cutting instrument through the angled cutting slot to cut the first metatarsal further comprises cutting a wedge-shaped section of bone from the first metatarsal.

13. The method of claim 1, wherein the angled cutting slot has a width within a range from 0.1 mm to 3 mm.

14. The method of claim 1, wherein the angled cutting slot is a first transverse cutting slot, and the cutting guide further comprises a second transverse cutting slot and a longitudinal cutting slot extending from the first transverse cutting slot to the second transverse cutting slot.

15. The method of claim 1, wherein guiding the cutting instrument through the angled cutting slot to cut the first metatarsal comprises making a first transverse cut across the first metatarsal, and further comprises making a second transverse cut with the cutting instrument across the first metatarsal.

16. The method of claim 1, wherein the cutting guide comprises a handle extending outwardly away from the body, and positioning the cutting guide against the medial side of the first metatarsal comprises manipulating the cutting guide with the handle.

17. The method of claim 1, wherein the cutting instrument comprises a saw blade.

18. The method of claim 1, wherein the cutting instrument comprises a burr.

19. The method of claim 1, wherein guiding the cutting instrument through the angled cutting slot to cut the first metatarsal comprises guiding the cutting instrument from the medial side of the first metatarsal through a lateral side of the first metatarsal.

20. The method of claim 1, wherein the angled cutting slot comprises a first transverse cutting slot, and the cutting guide further comprises a second transverse cutting slot offset from the first transverse cutting slot along a length of the first metatarsal.

* * * * *